United States Patent
Chao et al.

(10) Patent No.: US 9,954,189 B2
(45) Date of Patent: Apr. 24, 2018

(54) ORGANIC METAL COMPOUND AND ORGANIC LIGHT-EMITTING DEVICE EMPLOYING THE SAME

(71) Applicant: INDUSTRIAL TECHNOLOGY RESEARCH INSTITUTE, Hsinchu (TW)

(72) Inventors: Teng-Chih Chao, Hsinchu (TW); Ching-Hui Chou, New Taipei (TW); Han-Cheng Yeh, Taipei (TW); Meng-Hao Chang, New Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 358 days.

(21) Appl. No.: 14/833,976

(22) Filed: Aug. 24, 2015

(65) Prior Publication Data
US 2016/0164006 A1 Jun. 9, 2016

(30) Foreign Application Priority Data

Dec. 3, 2014 (TW) .............................. 103141946 A
Mar. 4, 2015 (TW) .............................. 104106786 A

(51) Int. Cl.
H01L 51/54 (2006.01)
C09K 11/06 (2006.01)
H01L 51/00 (2006.01)
C07F 15/00 (2006.01)
C09K 11/02 (2006.01)
H01L 51/50 (2006.01)

(52) U.S. Cl.
CPC ...... *H01L 51/0085* (2013.01); *C07F 15/0033* (2013.01); *C09K 11/025* (2013.01); *C09K 11/06* (2013.01); *C09K 2211/1007* (2013.01); *C09K 2211/1037* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 6,830,828 B2 | 12/2004 | Thompson et al. |
| 7,445,857 B2 | 11/2008 | Shen et al. |
| 7,781,077 B2 | 8/2010 | Yang et al. |
| 7,790,888 B2 | 9/2010 | Bold et al. |
| 8,173,274 B2 | 5/2012 | Lin et al. |
| 8,277,957 B2 | 10/2012 | Huang et al. |
| 8,324,800 B2 | 12/2012 | Royster, Jr. et al. |
| 8,431,243 B2 | 4/2013 | Kwong et al. |
| 8,475,936 B2 | 7/2013 | Huang et al. |
| 8,486,544 B2 | 7/2013 | Huang et al. |
| 8,722,207 B2 | 5/2014 | Huang et al. |
| 8,741,446 B2 | 6/2014 | Lin et al. |
| 8,871,360 B2 | 10/2014 | Huang et al. |
| 9,051,266 B2 | 6/2015 | Lin et al. |
| 2001/0019782 A1 | 9/2001 | Igarashi et al. |
| 2003/0072964 A1 | 4/2003 | Kwong et al. |
| 2006/0134462 A1 | 6/2006 | Yeh et al. |
| 2007/0237981 A1 | 10/2007 | Shen et al. |
| 2010/0295032 A1 | 11/2010 | Kwong et al. |
| 2011/0227049 A1 | 9/2011 | Xia et al. |
| 2011/0284799 A1 | 11/2011 | Stoessel et al. |
| 2011/0285275 A1 | 11/2011 | Huang et al. |

(Continued)

FOREIGN PATENT DOCUMENTS

CN 1589307 A 3/2005
CN 102453027 A 5/2012

(Continued)

OTHER PUBLICATIONS

Chang et al., "Unmodified small-molecule organic light-emitting diodes by blade coating", Organic Electronics, vol. 13, 2012, pp. 2149-2155.
Fan et al., "Highly efficient, solution-processed Orange-red phosphorescent OLEDs by using new iridium phosphor with thieno [3,2-c] pyridine derivative as cyclometalating ligand", Organic Electronics vol. 14, 2013, pp. 3392-3398.
Huang et al., "Uniform dispersionof triplet emitters in multi-layer solution-processed organic light-emitting diodes", Synthetic Metals, vol. 160, 2010, pp. 2393-2396.
Peng et al., "Highly efficient phosphorescent OLEDs with host-independent and concentration-insensitive properties based on a bipolar iridium complex", Journal of Materials Chemistry C, Feb. 27, 2013, vol. 1, pp. 2920-2926.

(Continued)

*Primary Examiner* — Marie R. Yamnitzky
(74) *Attorney, Agent, or Firm* — Birch, Stewart, Kolasch & Birch, LLP

(57) ABSTRACT

Organic metal compounds and organic electroluminescence devices employing the same are provided. The organic metal compound has a chemical structure represented below:

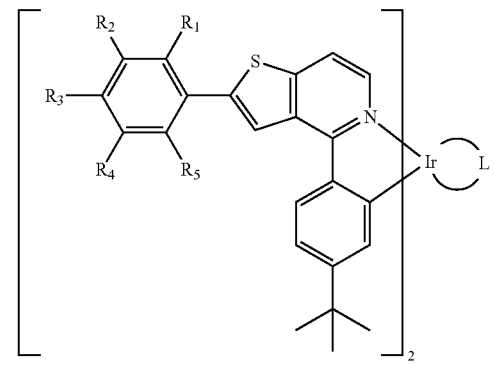

Formula (I)

wherein $R_1$, $R_2$, $R_3$, $R_4$, and $R_5$ are independent and can be hydrogen, halogen, $C_{1-8}$ alkyl or $C_{1-8}$ alkoxy; L can be acetylacetone ligand, picolinic acid ligand, N, N'-diisopropylbenzamidinate, or N, N'-diisopropyl-diisopropyl-guanidinate.

20 Claims, 1 Drawing Sheet

(56) References Cited

U.S. PATENT DOCUMENTS

| | | |
|---|---|---|
| 2012/0061654 A1 | 3/2012 | Rayabarapu et al. |
| 2012/0119190 A1 | 5/2012 | Alleyne et al. |
| 2012/0181511 A1 | 7/2012 | Ma et al. |
| 2012/0212126 A1 | 8/2012 | Tsai et al. |
| 2012/0217868 A1 | 8/2012 | Ma et al. |
| 2013/0032786 A1 | 2/2013 | Huang et al. |
| 2013/0033171 A1 | 2/2013 | Huang et al. |
| 2013/0033172 A1 | 2/2013 | Huang et al. |
| 2013/0126831 A1 | 5/2013 | Ma et al. |
| 2013/0146848 A1 | 6/2013 | Ma et al. |
| 2014/0103305 A1 | 4/2014 | Ma et al. |
| 2014/0124752 A1 | 5/2014 | Huang et al. |
| 2014/0131670 A1 | 5/2014 | Lin et al. |
| 2015/0123082 A1 | 5/2015 | Chi et al. |
| 2015/0188059 A1 | 7/2015 | Chao et al. |
| 2015/0188060 A1 | 7/2015 | Chao et al. |
| 2016/0164006 A1 | 6/2016 | Chao et al. |

FOREIGN PATENT DOCUMENTS

| | | |
|---|---|---|
| CN | 102911211 A | 2/2013 |
| CN | 102911212 A | 2/2013 |
| CN | 102952162 A | 3/2013 |
| CN | 103086949 A | 5/2013 |
| CN | 102190618 B | 9/2013 |
| CN | 103298907 A | 9/2013 |
| CN | 101659638 B | 10/2013 |
| CN | 102050794 B | 10/2013 |
| CN | 103804153 A | 5/2014 |
| CN | 102911162 B | 11/2014 |
| CN | 104628785 A | 5/2015 |
| CN | 102282150 B | 7/2015 |
| CN | 104744517 A | 7/2015 |
| JP | 5544390 B2 | 7/2014 |
| KR | 10-2014-0124654 A | 10/2014 |
| TW | I242999 B | 11/2005 |
| TW | 200621934 A | 7/2006 |
| TW | 200623955 A | 7/2006 |
| TW | 201127814 A1 | 8/2011 |
| TW | 201130948 A | 9/2011 |
| TW | 201141987 A1 | 12/2011 |
| TW | 201224114 A1 | 6/2012 |
| TW | 201233674 A1 | 8/2012 |
| TW | 201241152 A1 | 10/2012 |
| TW | 201307326 A1 | 2/2013 |
| TW | I385235 B | 2/2013 |
| TW | 201309714 A1 | 3/2013 |
| TW | I395804 B1 | 5/2013 |
| TW | 201326183 A1 | 7/2013 |
| TW | 201329199 A1 | 7/2013 |
| TW | 201329203 A1 | 7/2013 |
| TW | I402259 B1 | 7/2013 |
| TW | I421255 B | 1/2014 |
| TW | I425076 B | 2/2014 |
| TW | I429652 B | 3/2014 |
| TW | I431003 B | 3/2014 |
| TW | I440626 | 6/2014 |
| TW | I454450 B | 10/2014 |
| TW | 201446775 A | 12/2014 |
| TW | I471308 B | 2/2015 |
| TW | 201524984 A | 7/2015 |
| TW | 201524985 A | 7/2015 |
| WO | WO 2010/111175 A1 | 9/2010 |
| WO | WO 2010/118029 A1 | 10/2010 |

OTHER PUBLICATIONS

Peng et al., "Very highy-efficiency red-electrouminescence devices based on an amidinate-ligated phosphorescent iridium complex", Journal of Materials Chemistry, Oct. 12, 2009, vol. 19, pp. 8072-8074.

Son et al.,"Small single-triplet energy gap bipolar host materials for phosphorescent blue and white organic light emitting diodes", Journal of Materials Chemistry C, Jul. 22, 2013, vol. 1, pp. 5008-5014.

Yeh et al., "All-small-molecule efficient white organic light-emitting diodes by multi-layer blade coating", Organic Electronics, vol. 13, 2012, pp. 914-918.

U.S. Office Action for U.S. Appl. No. 14/837,844 dated Nov. 28, 2017.

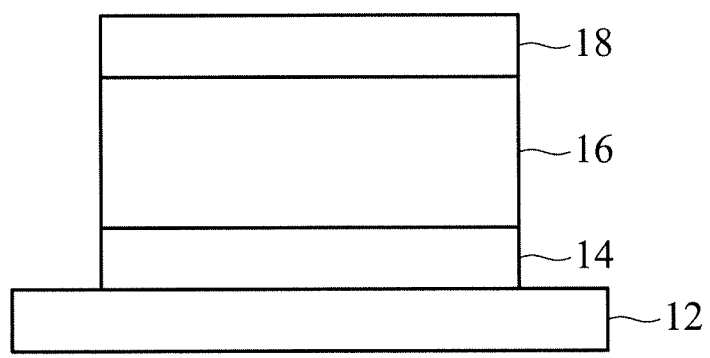

ORGANIC METAL COMPOUND AND ORGANIC LIGHT-EMITTING DEVICE EMPLOYING THE SAME

CROSS REFERENCE TO RELATED APPLICATIONS

The application is based on, and claims priorities from Taiwan Application Serial Number 103141946, filed on Dec. 3, 2014, and Taiwan Application Serial Number 104106786, filed on Mar. 4, 2015, the disclosure of which are hereby incorporated by reference herein in their entirety.

TECHNICAL FIELD

The disclosure relates to an organic metal compound and an organic light-emitting device employing the same.

BACKGROUND

Organic light-emitting diodes have superior characteristics over plasma display panels (PDPs) and inorganic electroluminescent display devices. These characteristics include low driving voltage (e.g., 10V or less), a broad viewing angle, rapid response time, and high contrast. Based on these advantages, organic light-emitting diodes can be used as pixels in graphic displays, television-image displays, and surface light sources. In addition, organic light-emitting diodes can be fabricated on flexible transparent substrates; they can be reduced in thickness and weight, and have good color representation. Therefore, the potential for organic light-emitting diodes to be used in next-generation flat-panel displays (FPDS) has been recognized.

A representative organic light-emitting diode was reported by Gurnee in 1969. However, this organic light-emitting diode suffers from limitations in its applications because of its limited performance. Since Eastman Kodak Co. reported multilayer organic light-emitting diodes in 1987, remarkable progress has been made in the development of organic light-emitting diodes capable of overcoming the problems of devices used in the prior art.

Such organic light-emitting diodes comprise a first electrode as a hole injection electrode (anode), a second electrode as an electron injection electrode (cathode), and an organic light-emitting layer disposed between the anode and the cathode wherein electrons injected from the cathode and holes injected from the anode combine with each other in the organic light-emitting layer to form electron-hole pairs (excitons), and then the excitons fall from the excited state to the ground state and decay to emit light. At this time, the excitons may fall from the excited state to the ground state via the singlet excited state to emit light (i.e. fluorescence), or the excitons may fall from the excited state to the ground state via the triplet excited state to emit light (i.e. phosphorescence). In the case of fluorescence, the probability of the singlet excited state is 25% and thus the luminescence efficiency of the devices is limited. In contrast, phosphorescence can utilize both probabilities of the triplet excited state (75%) and the singlet excited state (25%), and thus the theoretical internal quantum efficiency may reach 100%. Therefore, it is necessary to develop novel phosphorescent compounds suitable for phosphorescent OLEDs to enhance the luminous efficiency.

An OLED is typically categorized as either a micro-molecular OLED or a high-molecular OLED, according to its material type. At present, since micro-molecular OLEDs have a relatively higher efficiency, brightness, and lifetime than high-molecular OLEDs, the use of micro-molecular OLEDs is a trend in the OLED field. A micro-molecular OLED is generally fabricated by way of vacuum evaporation, so that the micro-molecular materials have good film forming qualities. However, 95% of the organic electroluminescent materials are deposited on the chamber wall of the manufacturing equipment used to manufacture the OLED, such that only 5% of the organic electroluminescent materials are coated on a substrate after the manufacturing process, resulting in a high investment cost. Therefore, a wet process (such as spin coating or blade coating) has been provided to fabricate micro-molecular OLEDs to improve the utilization ratio of organic electroluminescent materials and reduce the cost of manufacturing OLEDs. Unfortunately, conventional phosphorescent organic electroluminescent materials are not suitable to be used in the wet process due to their inferior solubility.

Therefore, it is necessary to develop novel phosphorescent organic compounds suitable for use in a wet process to fabricate phosphorescent OLEDs to solve the above problems.

SUMMARY

According to an embodiment of the disclosure, the disclosure provides an organic metal compound having Formula (I):

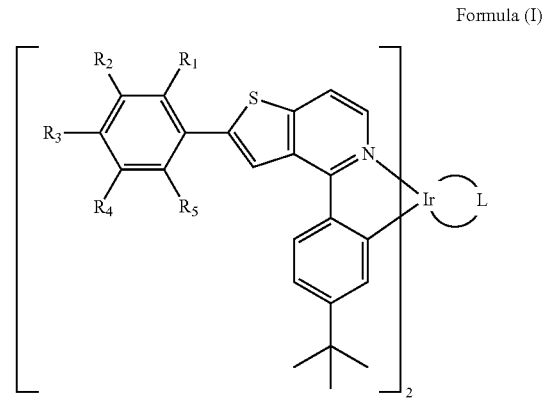

Formula (I)

wherein, $R_1$, $R_2$, $R_3$, $R_4$, and $R_5$ are independently hydrogen, halogen, $C_{1-8}$ alkyl group, or $C_{1-8}$ alkoxy group; L is acetylacetone ligand (acetylacetone ligand), picolinic acid ligand (picolinic ligand), N, N'-diisopropylbenzamidinate ligand, or N, N'-diisopropyl-diisopropyl-guanidinate ligand.

According to another embodiment of the disclosure, the disclosure provides an organic light-emitting device. The device includes a pair of electrodes and an organic light-emitting element disposed between the electrodes, wherein the organic light-emitting element includes the aforementioned organic metal compound.

According to another embodiment of the disclosure, the disclosure provides an organic light-emitting device. The device includes a pair of electrodes and an organic light-emitting element disposed between the electrodes, wherein the organic light-emitting element includes a light-emitting layer. The light-emitting layer includes a host material and a dopant material, wherein the dopant material includes the aforementioned organic metal compound.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 The FIGURE shows a cross section of an organic light-emitting device disclosed by an embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

According to an embodiment of the disclosure, the disclosure provides an organic metal compound having a structure as defined by Formula (I):

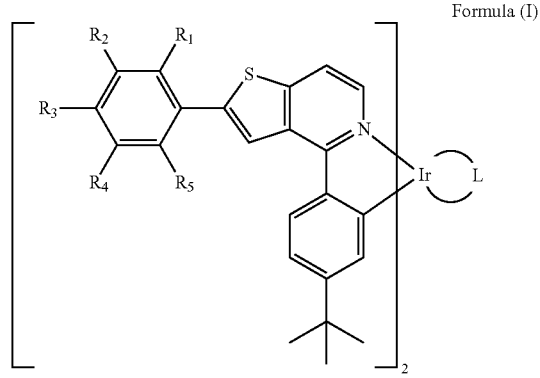

Formula (I)

wherein, $R_1$, $R_2$, $R_3$, $R_4$, and $R_5$ can be independently hydrogen, halogen, ($C_{1-8}$ alkyl group, or $C_{1-8}$ alkoxy group; L can be acetylacetone ligand, picolinic acid ligand, N, N'-diisopropylbenzalnidinate ligand, or N, N'-diisopropyl-diisopropyl-guanidinate ligand.

According to an embodiment of the disclosure, the disclosure also provides an organic metal compound having a structure as defined by Formula (II):

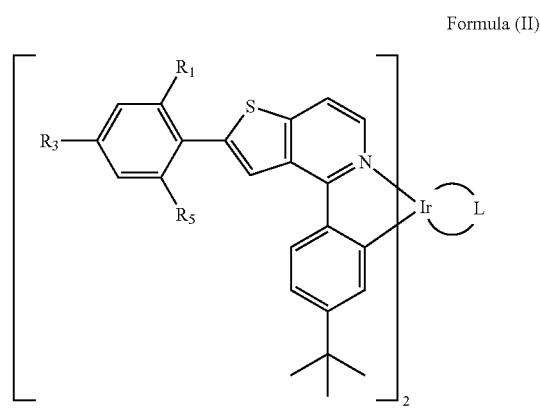

Formula (II)

wherein, $R_1$ and $R_5$ can be independently hydrogen, halogen, $C_{1-8}$ alkyl group, or $C_{1-8}$ alkoxy group; $R_3$ can be halogen, $C_{1-8}$ alkyl group (such as tert-butyl group), or $C_{1-8}$ alkoxy group; L can be acetylacetone ligand, picolinic acid ligand, N, N'-diisopropylbenzamidinate ligand, or N, N'-diisopropyl-diisopropyl-guanidinate ligand.

According to an embodiment of the disclosure, the disclosure also provides an organic metal compound having a structure as defined by Formula (III):

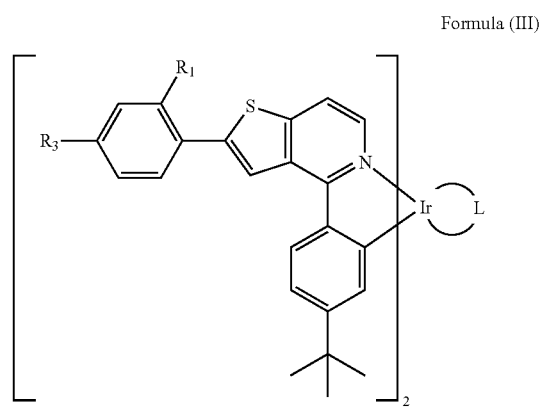

Formula (III)

wherein, $R_1$ can be hydrogen, halogen, $C_{1-8}$ alkyl group, or $C_{1-8}$ alkoxy group, $R_3$ can be halogen, $C_{1-8}$ alkyl group (such as tert-butyl group), or $C_{1-8}$ alkoxy group; L can be acetylacetone ligand, picolinic acid ligand, N, N'-diisopropylbenzamidinate ligand, or N, N'-diisopropyl-diisopropyl-guanidinate ligand.

According to an embodiment of the disclosure, when the organic metal compound having Formula (I), (II), or (III) has a halogen atom, the halogen atom can be fluorine. Further, the $C_{1-8}$ alkyl group of the organic metal compound of the disclosure can be isobutyl group, or tert-butyl group.

The organic metal compounds according to Formula (I) of the invention comprise the compounds shown in Table 1.

TABLE 1

| Example | Structure | organic metal compound |
|---|---|---|
| 1 | 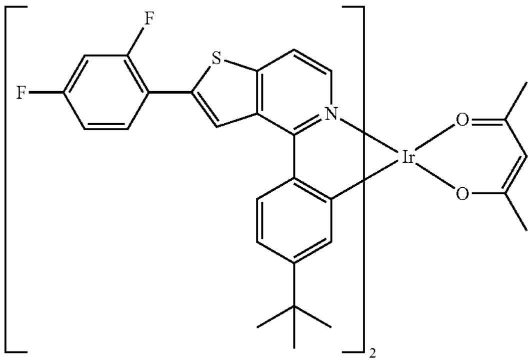 | organic metal compound (I) |
| 2 | 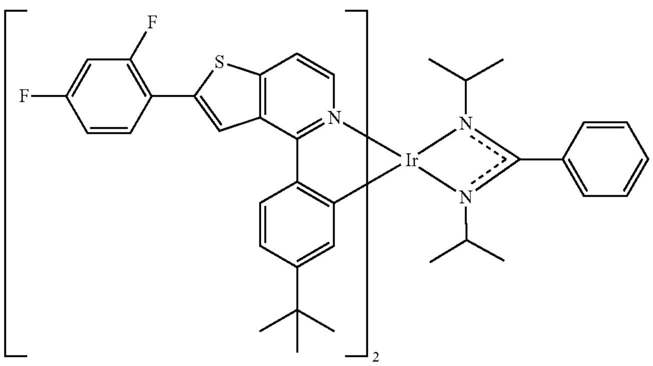 | organic metal compound (II) |
| 3 | 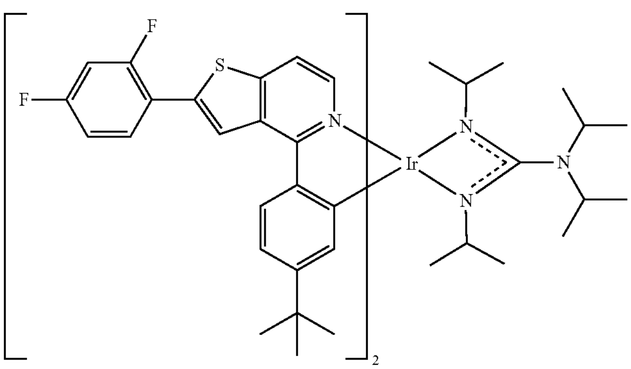 | organic metal compound (III) |
| 4 | 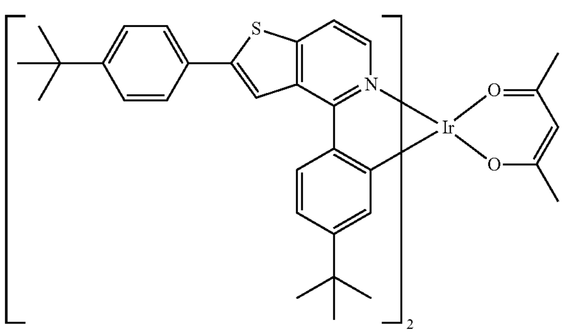 | organic metal compound (IV) |

TABLE 1-continued

| Example | Structure | organic metal compound |
|---|---|---|
| 5 | 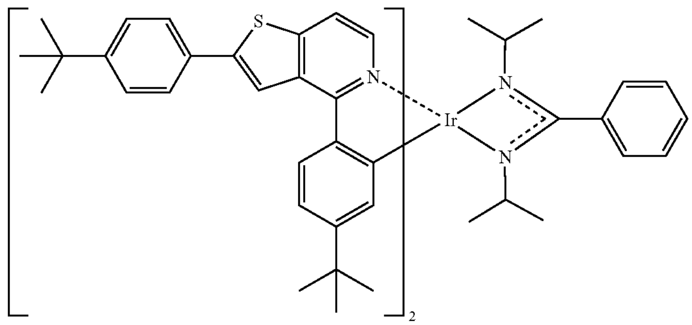 | organic metal compound (V) |
| 6 | 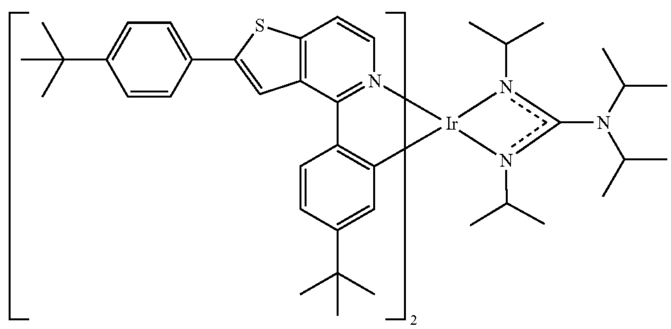 | organic metal compound (VI) |
| 7 | 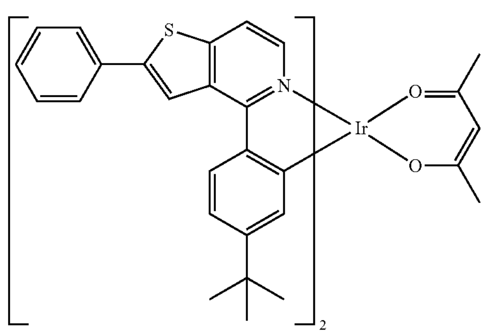 | organic metal compound (VII) |
| 8 | 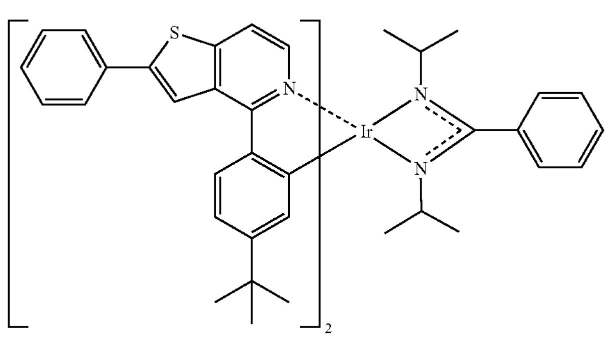 | organic metal compound (VIII) |

TABLE 1-continued

| Example | Structure | organic metal compound |
|---|---|---|
| 9 | 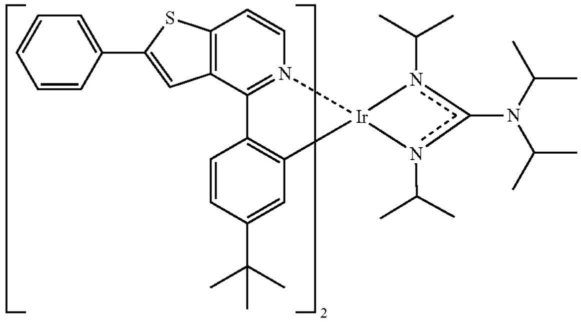 | organic metal compound (IX) |
| 10 | 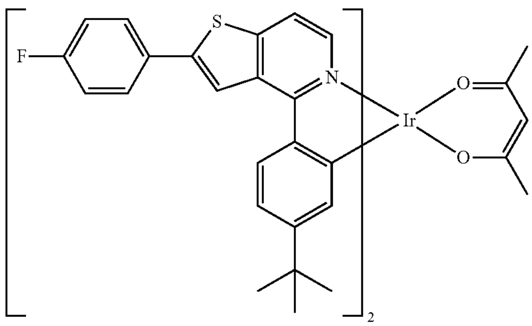 | organic metal compound (X) |
| 11 | 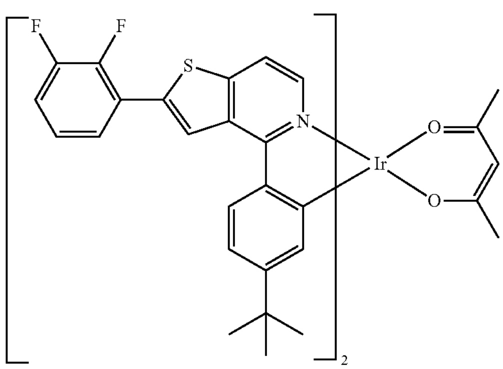 | organic metal compound (XI) |
| 12 | 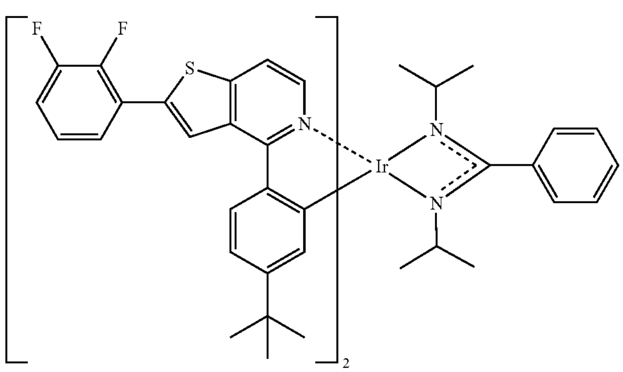 | organic metal compound (XII) |

TABLE 1-continued

| Example | Structure | organic metal compound |
|---|---|---|
| 13 | 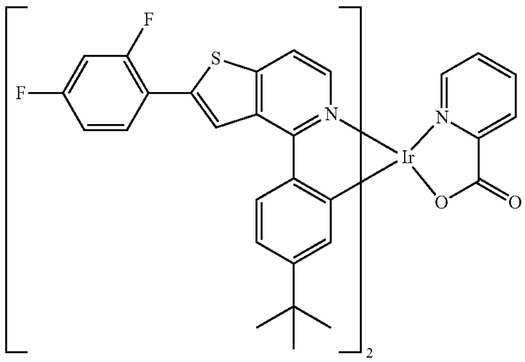 | organic metal compound (XIII) |
| 14 | 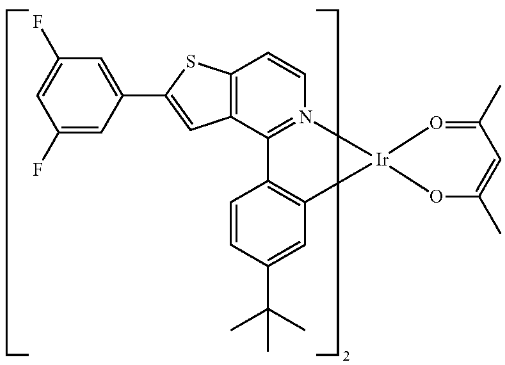 | organic metal compound (XIV) |
| 15 | 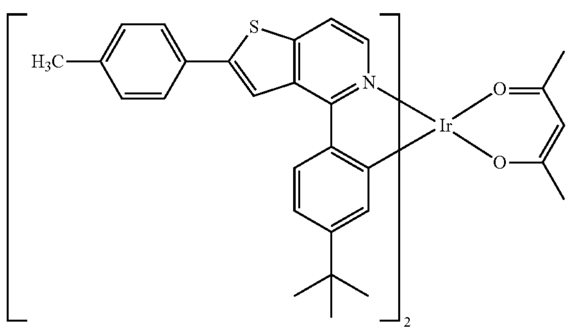 | organic metal compound (XV) |

The FIGURE shows an embodiment of an organic light-emitting device 10. The organic light-emitting device 10 includes a substrate 12, a bottom electrode 14, an organic light-emitting element 16, and a top electrode 18, as shown in the FIGURE. The organic light-emitting device can be a top-emission, bottom-emission, or dual-emission device. The substrate 12 can be a glass, plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Furthermore, at least one of the bottom and top electrodes 14 and 18 is transparent.

The organic light-emitting element 16 at least includes an emission layer, and can further include a hole injection layer, a hole transport layer, an electron transport layer, and an electron injection layer. In an embodiment of the disclosure, at least one layer of the organic light-emitting element 16 includes the aforementioned organometallic compound.

According to embodiments of the disclosure, the organic light-emitting element 16 can emit blue or green light under a bias voltage.

According to another embodiment of the disclosure, the organic light-emitting device can be a phosphorescent organic light-emitting device, and the emission layer of the organic light-emitting element can include a host material and a dopant, wherein the dopant can include the aforementioned organic metal compounds. The dose of the dopant is not limited and can be optionally modified by a person with ordinary skill in the field.

In order to clearly disclose the organic light-emitting devices of the disclosure, the following examples (employing the organic metal compounds of the disclosure) are intended to illustrate the disclosure more fully without limiting their scope, since numerous modifications and variations will be apparent to those skilled in this art. For example, when the organic metal compounds of the disclosure serves as a dopant material, the organic metal com-

Example 1: Preparation of Organic Metal Compound (I)

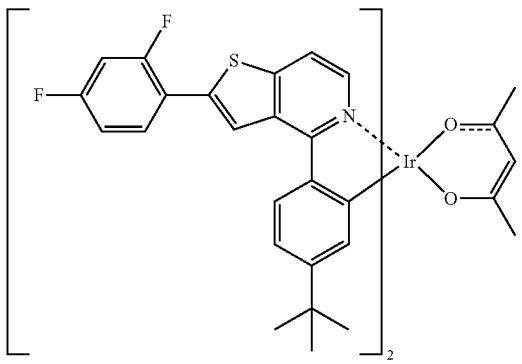

Organic metal compound (I)

34.89 g of 2-(2-aminoethyl)thiophene (compound (I)) (274.8 mmol) and 200 mL of water were added into a reaction bottle after removing moisture and purging nitrogen gas several times. Next, after cooling to 0° C., 45 g of 4-tert-butylbenzoyl chloride (compound (II)) (229 mmol) was added into the reaction bottle, and then a white solid was obtained. Next, NaOH aqueous solution (20%) was added into the reaction bottle and stirred for 8 hours. After filtration, a compound (III) (white solid) was obtained with a yield of 95%. The synthesis pathway of the above reaction was as follows:

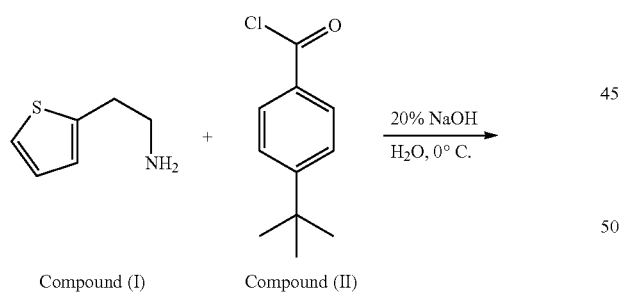

Compound (I)    Compound (II)

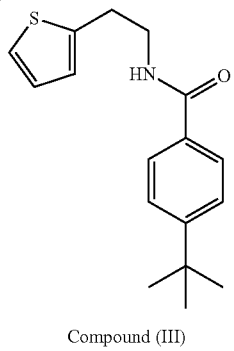

Compound (III)

The physical measurement of the compound (III) is listed below: $^1$H NMR (CDCl$_3$, 200 MHz) δ 7.67 (d, J=8.4 Hz, 2H), 7.43 (d, J=8.4 Hz, 2H), 7.20 (d, J=3.2 Hz, 1H), 6.97 (q, J=8.0, 3.6 Hz, 1H), 6.88 (d, J=3.2 Hz, 1H), 6.24 (s, 1H), 7.73 (q, J=6.2 Hz, 2H), 3.15 (t, J=6.2 Hz, 2H), 1.34 (s, 9H).

Next, the compound (III) (12 g, 41.81 mmol) and toluene (175 mL) were added into a 250 mL reaction bottle. The reaction bottle was placed in an ice water bath, and phosphoryl chloride (POCl$_3$) (11.7 mL, 125.43 mmol) was added into the reaction bottle. After the addition was complete, the reaction bottle was heated to reflux. After refluxing for 2 hr, saturated sodium hydrogen carbonate (NaHCO$_3$) aqueous solution was added to neutralize the reaction, and then the mixture was extracted with toluene. Next, an organic phase was separated and concentrated, and then dried by anhydrous magnesium sulfate. After concentration using a rotary evaporator, the result was left to stand for several hours, obtaining a compound (IV) (crystalline) with a yield of 98%. The synthesis pathway of the above reaction was as follows:

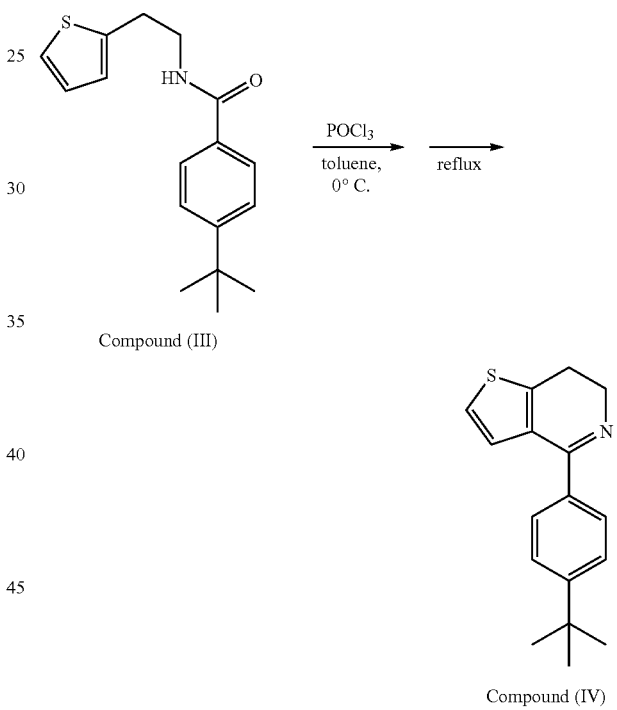

The physical measurement of the compound (IV) is listed below: $^1$H NMR (CDCl$_3$, 200 MHz) δ 7.96 (d, J=8.4 Hz, 2H), 7.64 (d, J=8.4 Hz, 2H), 7.38 (d, J=5.6 Hz, 1H), 7.27 (d, J=5.8 Hz, 1H), 3.95 (t, J=8.0 Hz, 2H), 3.32 (t, J=8.0 Hz, 2H), 1.36 (s, 9H).

Next, the compound (IV) (11 g, 40.89 mmol), 10 g palladium 10% on carbon (Pd/C), and 100 mL of xylene were added into a reaction bottle. Next, the reaction bottle was heated to reflux. After reacting for 48 hours, Pd/C was removed by diatomaceous earth filter aid (Celite 545), and the filtrate was concentrated by a rotary evaporator. After purification by column chromatography with ethyl acetate and hexane (1:5), a compound (V) with a yield of 92% was obtained. The synthesis pathway of the above reaction was as follows:

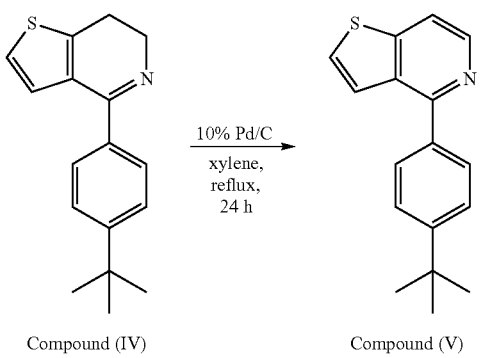 [SMILES: CC(C)(C)c1ccc(C2=NCCc3sccc32)cc1 ; "10% Pd/C" ; CC(C)(C)c1ccc(-c2nccc3sccc23)cc1]

Compound (IV) → Compound (V)
(10% Pd/C, xylene, reflux, 24 h)

The physical measurement of the compound (V) is listed below: $^1$H NMR (CDCl$_3$, 200 MHz) δ 8.54 (d, J=5.4 Hz, 1H), 7.81 (s, 1H), 7.76 (t, J=2.6 Hz, 2H), 7.67 (d, J=5.4 Hz, 1H), 7.55 (d, J=6.6 Hz, 2H), 7.48 (d, J=5.8 Hz, 1H), 1.39 (s, 9H).

Next, 250 mL anhydrous tetrahydrofuran (THF), and the compound (V) (10.68 g, 40 mmol) were added into a reaction bottle, and then the reaction bottle was cooled to −78° C. Next, n-butyl lithium (n-BuLi) (30 mL, 48 mmol) was dropwisely added into the reaction bottle. After the addition was complete, the mixture was stirred for 1 hour. Next, I$_2$ (11.16 g, 44 mmol) was added into the reaction bottle at −78° C., and the mixture was stirred for 3 hours. Next, D.I. water was added into the reaction bottle, and the result was extracted with ethyl acetate as the extraction solvent. After purification by column chromatography (with ethyl acetate and hexane (1:10)), a compound (VI) with a yield of 99% was obtained. The synthesis pathway of the above reaction was as follows:

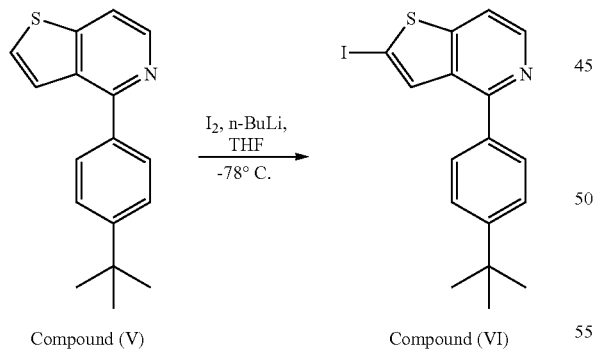

Compound (V) → Compound (VI)
(I$_2$, n-BuLi, THF, −78° C.)

The physical measurement of the compound (VI) is listed below: $^1$H NMR (CDCl$_3$, 200 MHz) δ 8.46 (d, J=5.6 Hz, 1H), 7.83 (s, 1H), 7.71 (d, J=8.6 Hz, 2H), 7.63 (d, J=5.8 Hz, 1H), 7.53 (d, J=8.0 Hz, 2H), 1.37 (s, 9H).

Next, the compound (VI) (15.67 g, 39.87 mmol), 2,4-difluorophenylboronic acid (compound (VII)) (12.59 g, 79.74 mmol), tetrakis(triphenyl phosphine) palladium (Pd(PPh$_3$)$_4$) (1.84 g, 1.595 mmol), potassium carbonate (K$_2$CO$_3$) (11.02 g, 79.74 mmol), 1,2-dimethoxyethane (DME) (53.3 mL), and water (26.7 mL) were added into a reaction bottle, and the reaction bottle was heated to 80° C. After cooling to room temperature, D.I. water was added into the reaction bottle, and the result was extracted with ethyl acetate as the extraction solvent. After purification by column chromatography (with ethyl acetate and hexane (1:40), a compound (VIII) with a yield of 78% was obtained. The synthesis pathway of the above reaction was as follows:

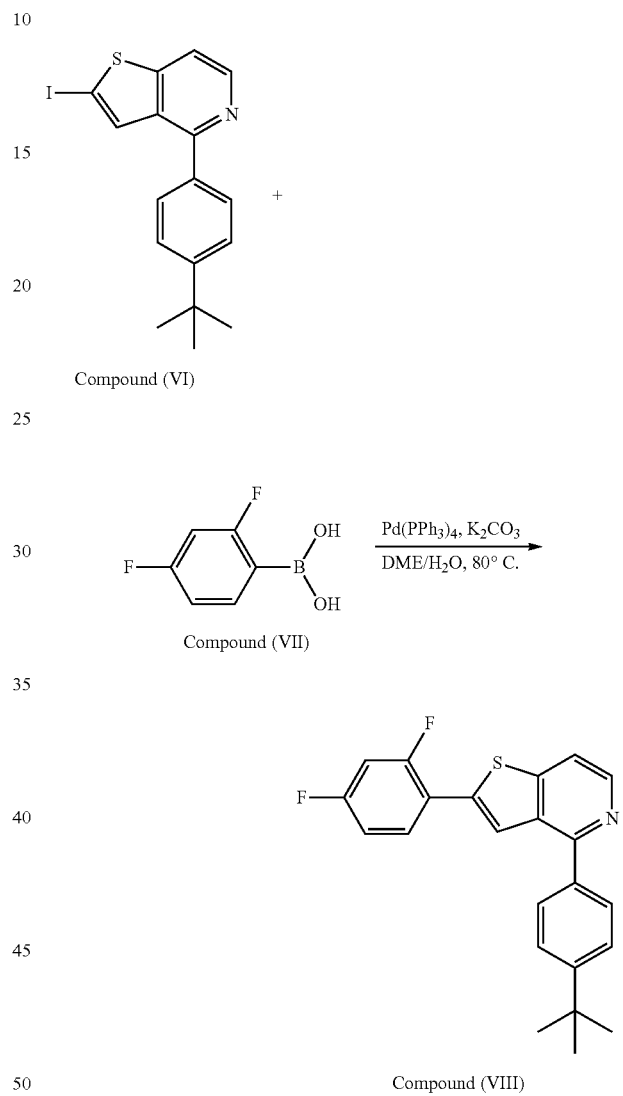

Compound (VI) + Compound (VII) → Compound (VIII)
(Pd(PPh$_3$)$_4$, K$_2$CO$_3$, DME/H$_2$O, 80° C.)

The physical measurement of the compound (VIII) is listed below: $^1$H NMR (CDCl$_3$, 200 MHz) δ 8.56 (d, J=5.6 Hz, 1H), 7.93 (s, 1H), 7.81 (d, J=8.0 Hz, 2H), 7.72 (d, J=5.6 Hz, 1H), 7.66 (d, J=6.6 Hz, 1H), 7.57 (d, J=7.6 Hz, 2H), 6.94 (m, 2H), 1.40 (s, 1H).

Next, the compound (VIII) (5 g, 13.19 mmol), IrCl$_3$.H$_2$O (1.787 g, 5.997 mmol), and 15 mL 2-methoxy ethanol and 5 mL of water were added into a reaction bottle, and the reaction bottle was heated to 140° C. After reacting for 24 hours, D.I. water was added into the reaction bottle. After filtration, a compound (IX) (orange solid) with a yield of 99% was obtained. The synthesis pathway of the above reaction was as follows:

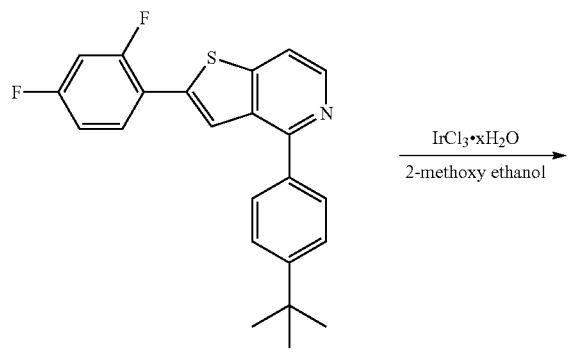

Compound (VIII)

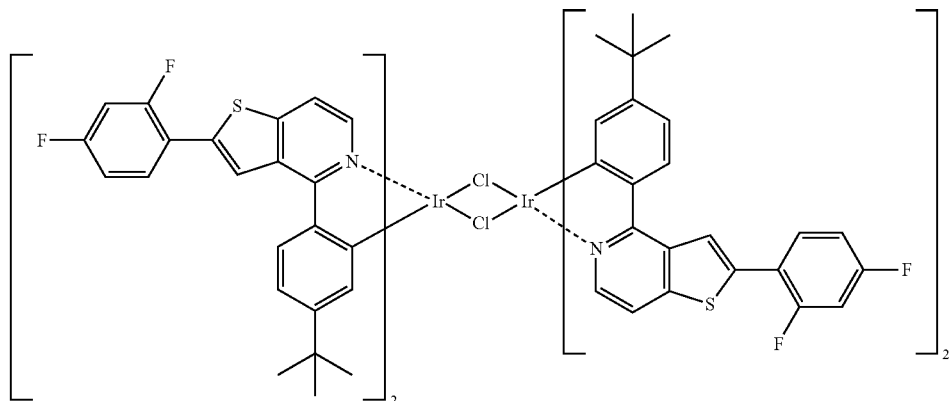

Compound (IX)

Next, the compound (IX) (6 g, 3.05 mmol), 2,4-pentanedione (12.21 g, 12.2 mmol), sodium carbonate (1.29 g, 12.2 mmol), and 30 mL of 2-methoxyethanol were added into a reaction bottle, and the reaction bottle was heated to 140° C. After reacting for 24 hours, the reaction bottle was cooled to room temperature, and D.I. water (50 mL) was added into the reaction bottle. After filtration, an orange mixture was obtained. After purification by column chromatography with dichloromethane and n-hexane (1:3), the organic metal compound (I) (orange solid) with a yield of 39% was obtained. The synthesis pathway of the above reaction was as follows:

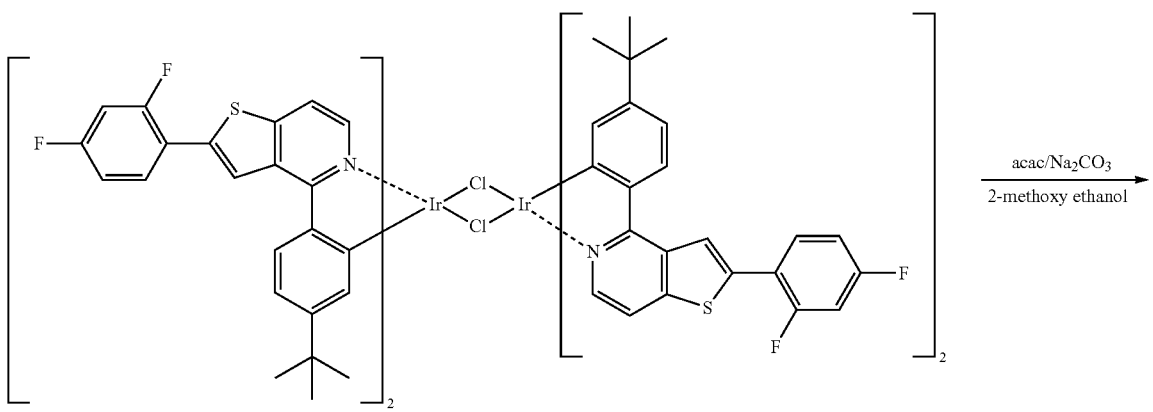

Compound (IX)

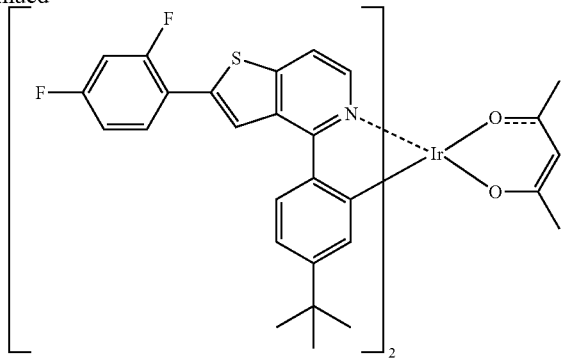

Organic metal compound (I)

The physical measurement of the organic metal compound (I) is listed below: $^1$H NMR (200 MHz, CDCl$_3$) δ 8.57 (s, 2H), 8.45 (d, J=6.6 Hz, 2H), 8.01 (d, J=8.6 Hz, 2H), 7.73~7.78 (dd, J=1.8 Hz, 2H), 7.59 (d, J=6.2 Hz, 2H), 6.90~7.07 (m, 6H), 6.29 (d, J=2.2 Hz, 2H), 5.22 (s, 1H), 1.79 (s, 6H), 0.92 (s, 18H).

Example 2: Preparation of Organic Metal Compound (II)

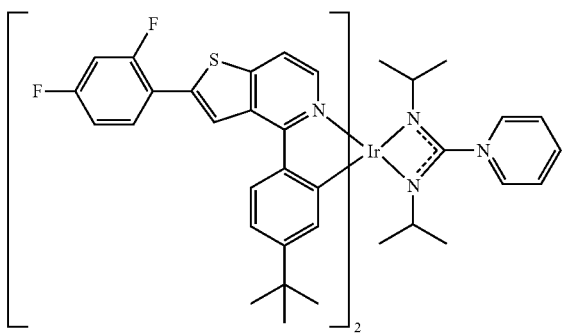

Organic metal compound (II)

50 mL of anhydrous tetrahydrofuran (THF), and bromnobenzene (compound (X)) (1.32 mL, 12.488 mmol) were added into a reaction bottle, and the reaction bottle was cooled to −78° C. Next, n-butyl lithium (n-BuLi) (7.8 mL, 12.488 mmol) was dropwisely added into the reaction bottle. After the addition was complete, the mixture was stirred for 30 minutes. N,N-diisopropylcarbodiimide (compound XI) (1.95 mL, 12.488 mmol) was dropwisely added into the reaction bottle at −78° C. After the addition was complete, the mixture was stirred for 30 minutes, obtaining a solution containing the compound (XII). The above solution was dropwisely added into a solution containing the compound (IX) (6.14 g, 3.122 mmol) dissolved in 70 mL of tetrahydrofuran (THF). After the addition was complete, the bottle was heated to reflux. After reacting for 8 hours, the result was concentrated. After purification by column chromatography with ethyl acetate and hexane (1:4), an organic metal compound (II) (red solid) with a yield of 58% was obtained. The synthesis pathway of the above reaction was as follows:

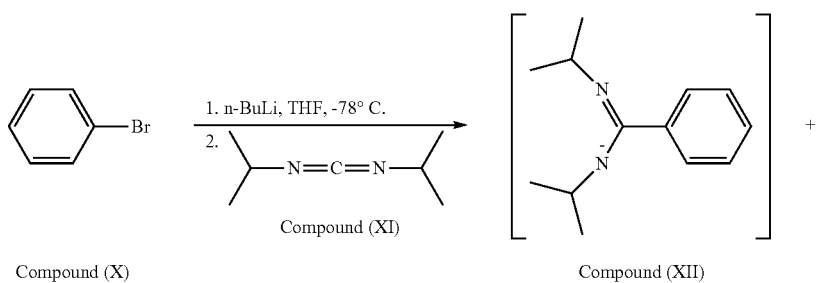

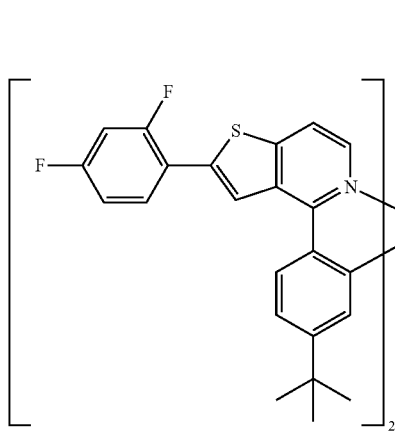
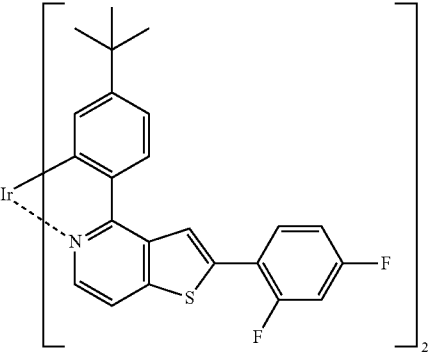

Compound (IX)

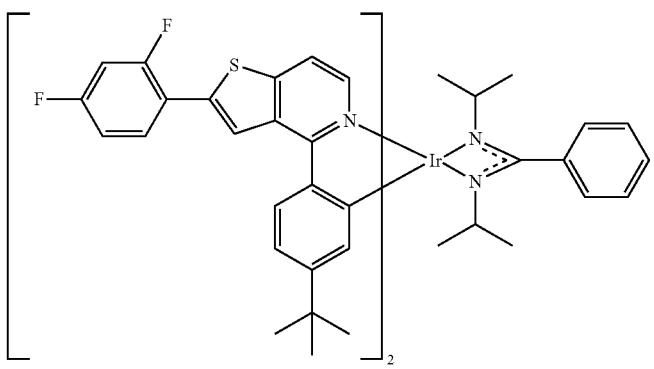

Organic metal compound (II)

The physical measurement of the organic metal compound (II) is listed below: $^1$H NMR (200 MHz, CDCl$_3$) δ 9.39 (d, J=6.2 Hz, 2H), 8.56 (s, 2H), 8.00 (d, J=8.4 Hz, 2H), 7.74~7.83 (m, 2H), 7.56 (d, J=8.4 Hz, 1H), 7.28~7.43 (m, 4H), 6.96~7.07 (m, 6H), 6.85 (dd, J=8.0, 2.2 Hz, 2H), 6.38 (d, J=1.8 Hz, 2H), 3.35 (m, 2H), 0.97 (s, 18H), 0.67 (d, J=6.2 Hz, 6H), −0.06 (d, J=6.2 Hz, 6H).

Example 3: Preparation of Organic Metal Compound (III)

Organic metal compound (III)

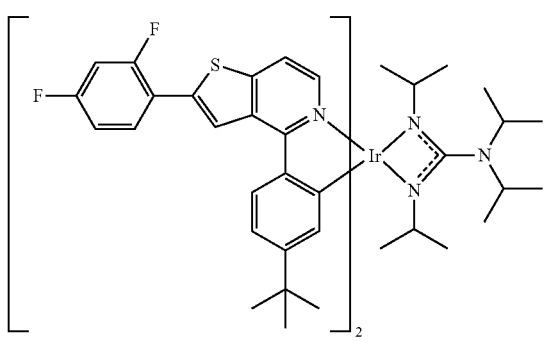

50 mL of anhydrous tetrahydrofuran (THF), and N,N-diisopropylcarbodiimide, compound (XI) (1.95 mL, 12.51 mmol) were added into a reaction bottle, and the reaction bottle was cooled to −78° C. Next, lithium diisopropylamide (LDA) (9.4 mL, 18.76 mmol) was dropwisely added into the reaction bottle. After the addition was complete, the mixture was stirred for 1 hour, obtaining a solution containing the compound (XIII). The above solution was dropwisely added into a solution including the compound (IX) (6.15 g, 3.13 mmol) and 70 mL of tetrahydrofuran (THF). After the addition was complete, the bottle was heated to reflux. After reacting for 8 hours, the result was concentrated. After purification by column chromatography with ethyl acetate and hexane (1:6), an organic metal compound (III) with a yield of 17% was obtained. The synthesis pathway of the above reaction was as follows:

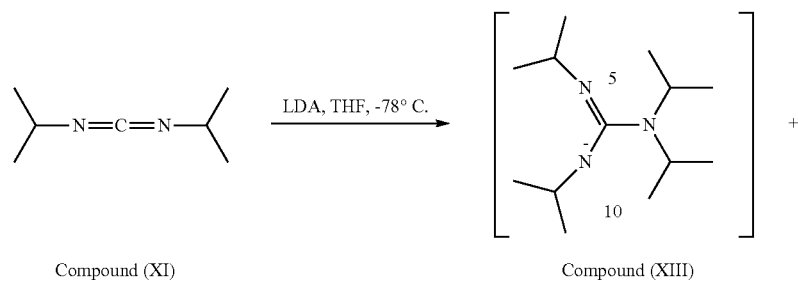
Compound (XI)  Compound (XIII)
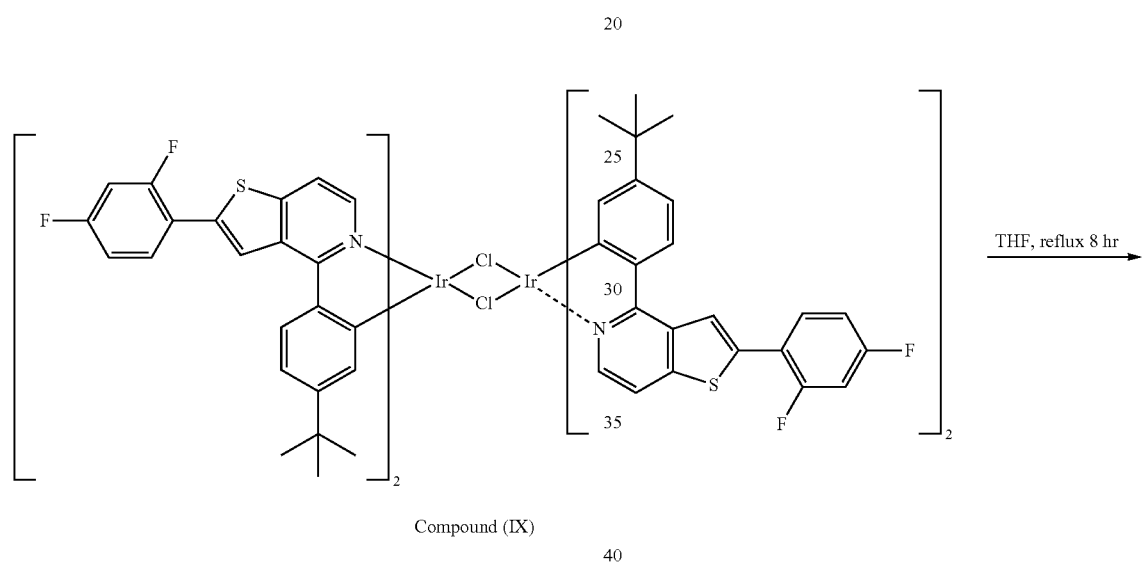
Compound (IX)
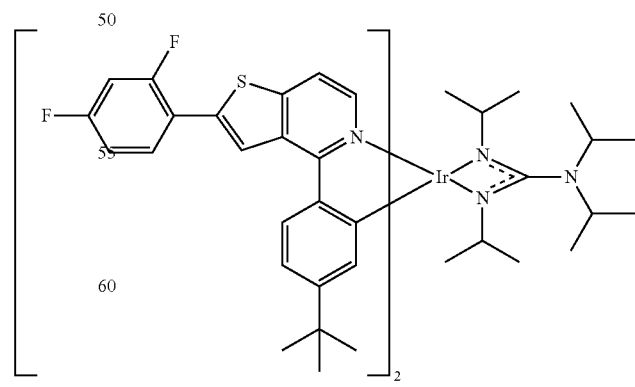
Organic metal compound (III)

The physical measurement of the organic metal compound (III) is listed below: $^1$H NMR (200 MHz, CDCl$_3$) δ 9.22 (d, J=6.2 Hz, 2H), 8.53 (s, 2H), 7.98 (d, J=8.4 Hz, 2H), 7.69~7.78 (m, 2H), 7.60 (d, J=6.2 Hz, 2H), 6.97~7.08 (m, 4H), 6.85 (dd, J=8.0, 1.8 Hz, 2H), 6.32 (s, 2H), 3.83 (m, 2H), 3.52 (m, 2H), 1.24 (m, 12H), 0.96 (s, 18H), 0.84 (d, J=6.2 Hz, 6H), −0.02 (d, J=6.2 Hz, 6H).

Example 4: Preparation of Organic Metal Compound (IV)

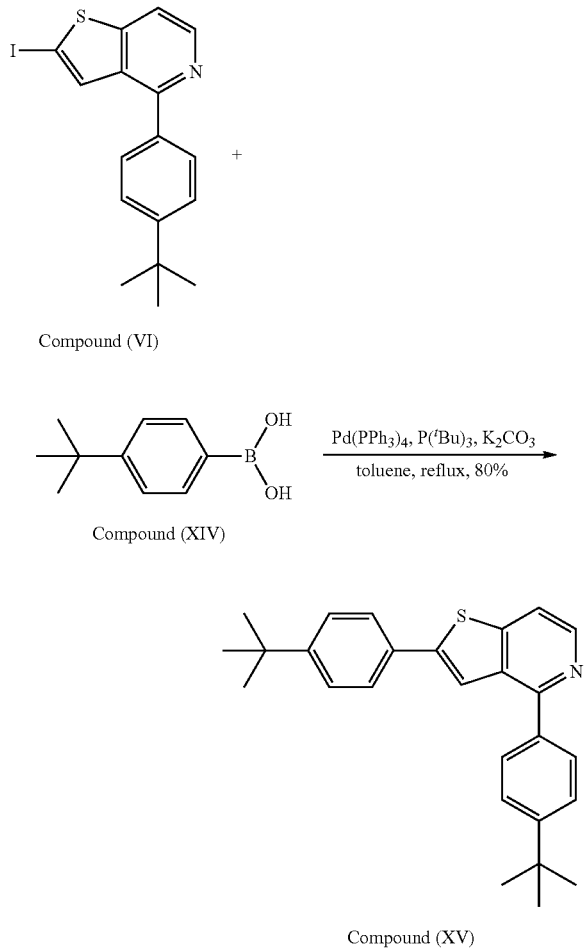

The compound (VI) (7.1 g, 18.1 mmol), the compound (XIV) (4-tert-butylphenylboronic acid) (3.86 g, 21.7 mmol), tri-tert-butylphosphine (0.1 g, 0.5 mmol), tetrakis(triphenyl phosphine) palladium (Pd(PPh$_3$)$_4$) (1.1 g, 0.95 mmol), potassium carbonate (K$_2$CO$_3$) aqueous solution (2M, 20 mL), and toluene (50 mL) were added into a reaction bottle, and the reaction bottle was heated to 110° C. After cooling to room temperature, D.I. water was added into the reaction bottle, and the result was extracted with ethyl acetate as the extraction solvent. After purification by column chromatography with ethyl acetate and hexane (1:40), a compound (XV) with a yield of 75% was obtained. The synthesis pathway of the above reaction was as follows:

The physical measurement of the compound (XV) is listed below: $^1$H NMR (CDCl$_3$, 200 MHz) δ 8.49 (d, J=5.4 Hz, 1H), 7.80 (d, J=8.8 Hz, 2H), 7.80 (s, 1H), 7.54-7.71 (m, 5H), 7.45 (d, J=8.6 Hz, 2H), 1.34 (s, 9H), 1.39 (s, 9H).

Next, the compound (XV) (6.3 g, 15.8 mmol) and IrCl$_3$·H$_2$O (2.14 g, 7.2 mmol), 15 mL of 2-methoxy ethanol and 5 mL, and water were added into a reaction bottle, and then the reaction bottle was heated to 140° C. After reacting for 24 hours, D.I. water was added into the reaction bottle. After filtration, a compound (XVI) (orange solid) with a yield of 87% was obtained. The synthesis pathway of the above reaction was as follows:

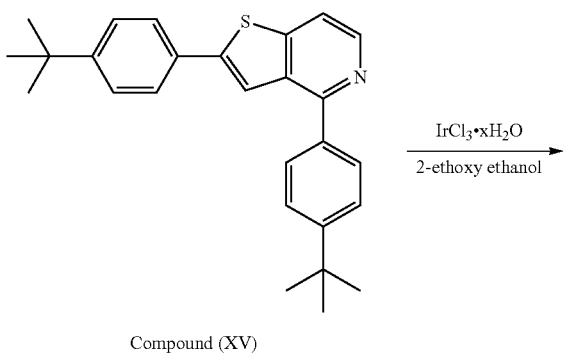

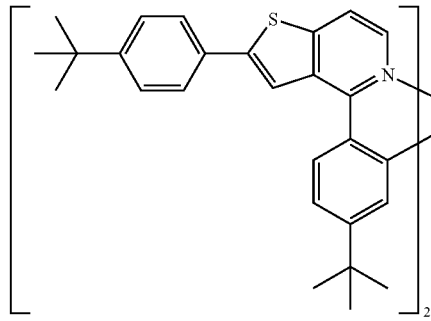

Compound (XVI)

Next, the compound (XVI) (7.0 g, 3.42 mmol), acetyl acetone (1.37 g, 13.68 mmol), and potassium carbonate (Na$_2$CO$_3$) (1.45 g, 13.68 mmol) were added into a reaction bottle. Next, 2-methoxy ethanol serving as solvent was added into the reaction bottle, and the reaction bottle was heated to reflux under nitrogen gas. After cooling to room temperature, five-fold water (by weight) was added into the reaction bottle and then an orange precipitate was obtained. After filtration, the result was extracted with water and dichloromethane. After purification by column chromatography, the organic metal compound (IV) (orange solid), with a yield of 58%. The synthesis pathway of the above reaction was as follows:

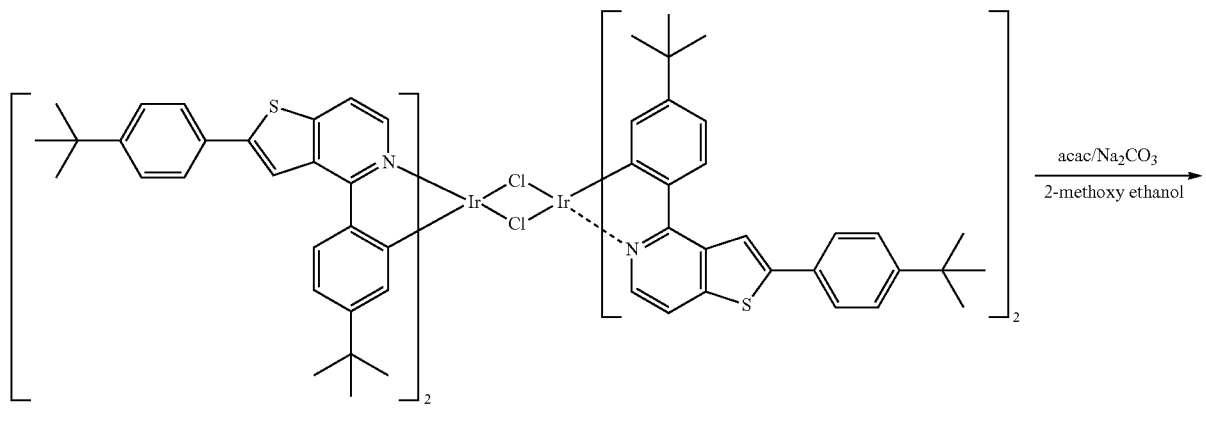

Compound (XVI)

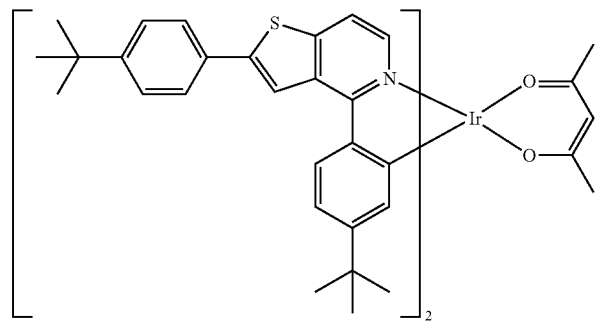

Organic metal compound (IV)

The physical measurement of the organic metal compound (IV) is listed below: $^1$H NMR (CDCl$_3$, 200 MHz) δ 8.41 (d, J=6.8 Hz, 2H), 8.04 (d, J=8.4 Hz, 1H), 7.7.4 (d, J=8.6 Hz, 2H), 7.50-7.60 (m, 3H), 6.92 (dd, J=8.4, 2.2 Hz, 1H), 6.28 (d, J=1.8 Hz, 1H), 5.23 (s, 1H), 1.77 (s, 6H), 1.40 (s, 9H), 1.00 (s, 9H).

Example 5: Preparation of Organic Metal Compound (V)

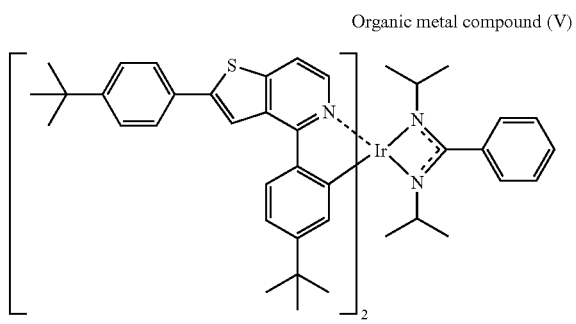

Organic metal compound (V)

50 mL of anhydrous tetrahydrofuran (THF), bromobenzene, the compound (X) (1.67 mL, 15.8 mmol) were added into a reaction bottle. After cooling to −78° C., n-butyl lithium (n-BuLi) was dropwisely added into the reaction bottle (9.98 mL, 15.8 mmol) at −78° C. After the addition was complete, the mixture was stirred for 30 minutes. N,N-diisopropylcarbodiimide, and the compound (XI) (2.47 mL, 15.8 mmol) was dropwisely added into the reaction bottle at −78° C. After the addition was complete, the mixture was stirred for 30 minutes, obtaining a solution containing the compound (XII). The above solution was dropwisely added into a solution including the compound (XVI) (8.1 g, 3.96 mmol) and 70 mL of tetrahydrofuran (THF). After the addition was complete, the bottle was heated to reflux. After reacting for 8 hours, the result was concentrated. After purification by column chromatography with ethyl acetate and hexane (1:4), an organic metal compound (V) (red solid), with a yield of 65%, was obtained. The synthesis pathway of the above reaction was as follows:

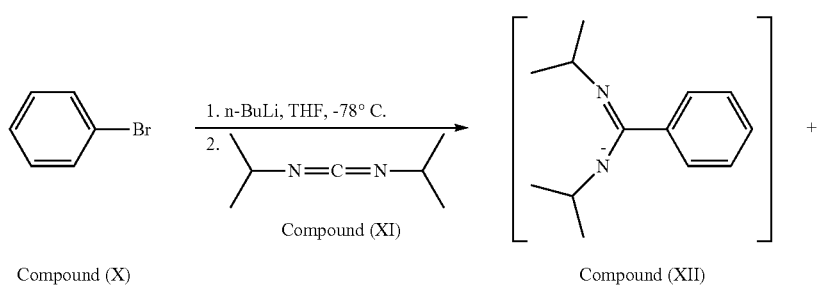

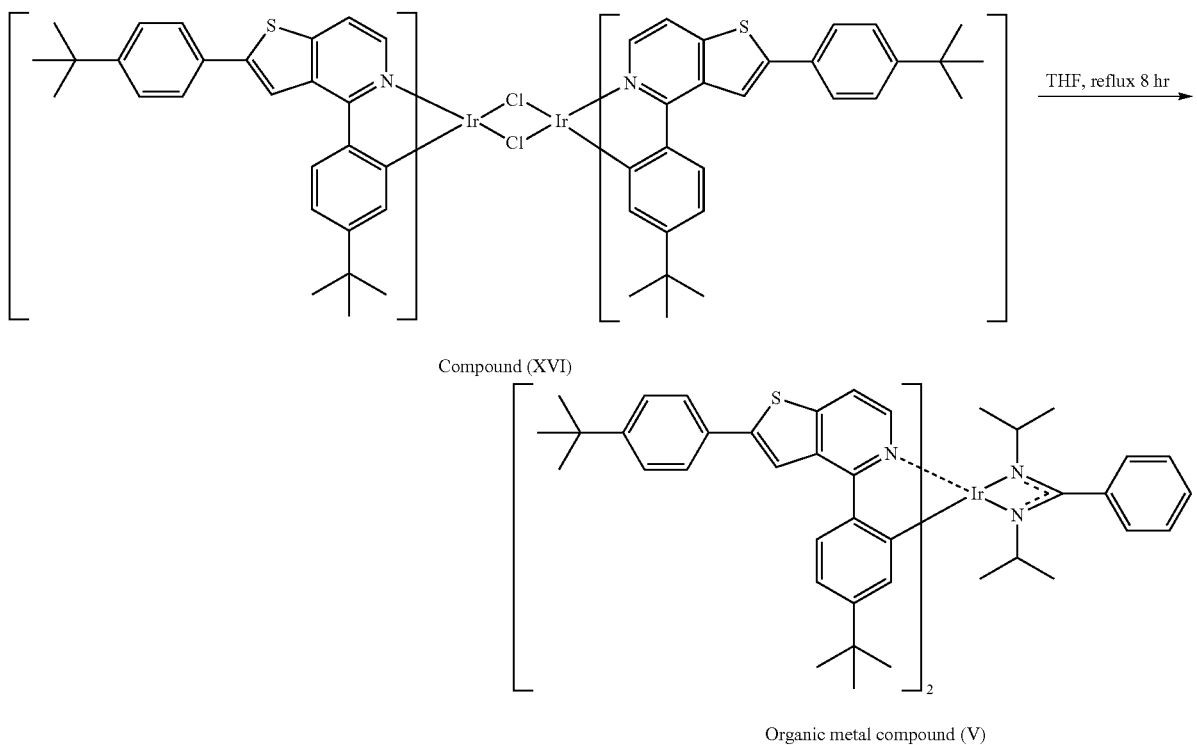

The physical measurement of the organic metal compound (V) is listed below: $^1$H NMR (200 MHz, CDCl$_3$) δ 9.35 (d, J=6.2 Hz, 2H), 8.45 (s, 2H), 8.02 (d, J=8.2 Hz, 2H), 7.74~7.83 (m, 2H), 7.56 (d, J=8.4 Hz, 1H), 7.28~7.43 (m, 4H), 6.96~7.07 (m, 6H), 6.85 (dd, J=8.0, 2.2 Hz, 2H), 6.38 (d, J=1.8 Hz, 2H), 0.97 (s, 18H), 0.67 (d, J=6.2 Hz, 6H), −0.06 (d, J=6.4 Hz, 6H).

Example 6: Preparation of Organic Metal Compound (VI)

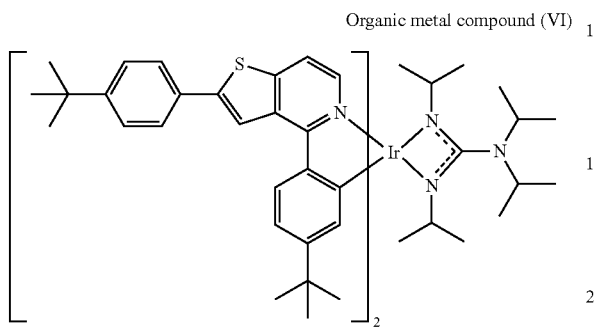

Organic metal compound (VI)

50 mL of anhydrous tetrahydrofuran (THF) and N,N-diisopropylcaroixlimide, 1.95 mL of the compound (XI) (12.51 mmol) were added into a reaction bottle. After cooling to −78° C., 9.4 mL of lithium diisopropylamide (LDA) (18.76 mmol) was dropwisely added into the reaction bottle. After the addition was complete, the mixture was stirred for 1 hour, obtaining a solution including a compound (XIII). The above solution was dropwisely added into a solution including a compound (XVI) (6.15 g, 3.13 mmol) and 70 mL of tetrahydrofuran (THF). After the addition was complete, the bottle was heated to reflux. After reacting for 8 hours, the result was concentrated. After purification by column chromatography with ethyl acetate and hexane (1:6), an organic metal compound (VI) (brown solid) with a yield of 57% was obtained. The synthesis pathway of the above reaction was as follows:

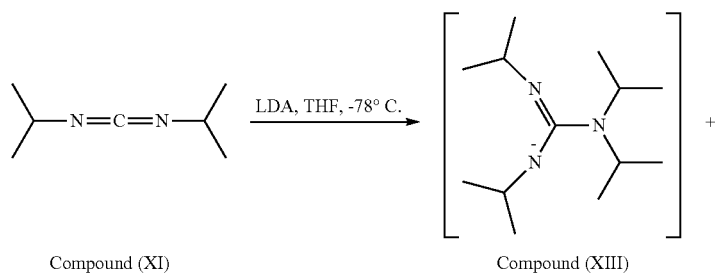

Compound (XI)                Compound (XIII)

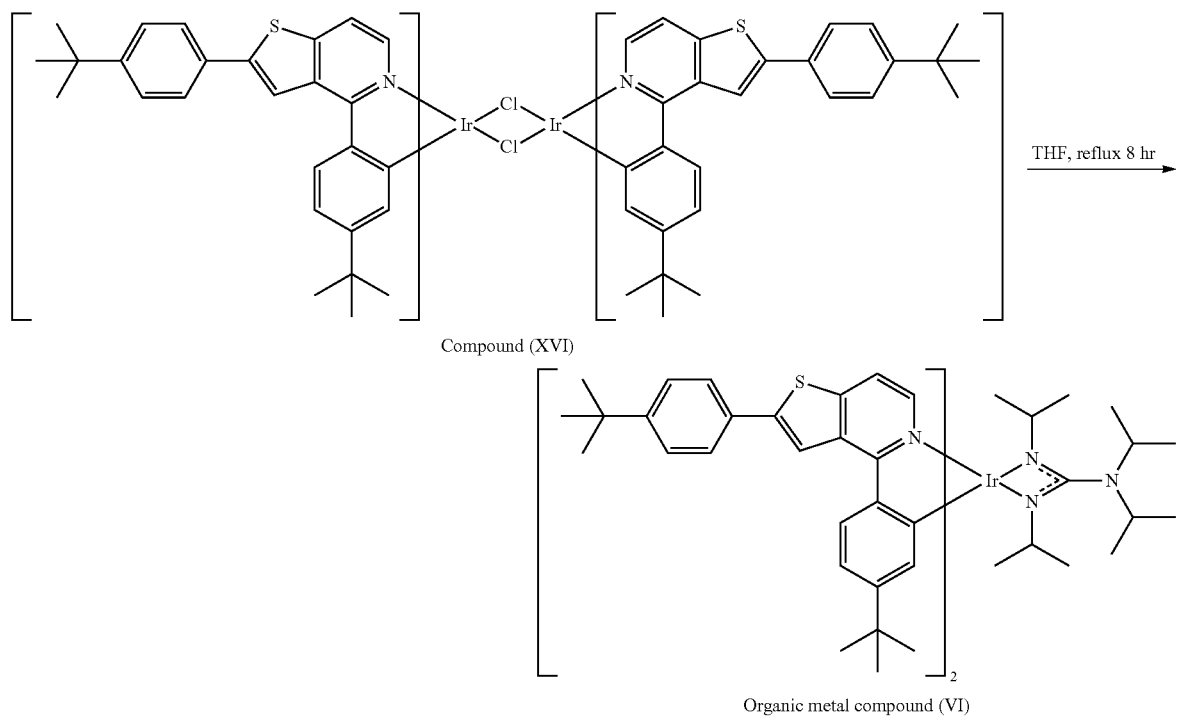

Compound (XVI)

Organic metal compound (VI)

The physical measurement of the organic metal compound (VI) is listed below: $^1$H NMR (200 MHz, CDCl$_3$) δ 9.22 (d, J=6.2 Hz, 2H), 8.53 (s, 2H), 7.98 (d, J=8.4 Hz, 2H), 7.69~7.78 (m, 2H), 7.60 (d, J=6.2 Hz, 2H), 6.97~7.08 (m, 4H), 6.85 (dd, J=8.0, 1.8 Hz, 2H), 6.32 (s, 2H), 3.83 (m, 2H), 3.52 (m, 2H), 1.24 (m, 12H), 0.96 (s, 18H), 0.84 (d, J=6.2 Hz, 6H), −0.02 (d, J=6.2 Hz, 6H).

Example 7: Preparation of Organic Metal Compound (VII)

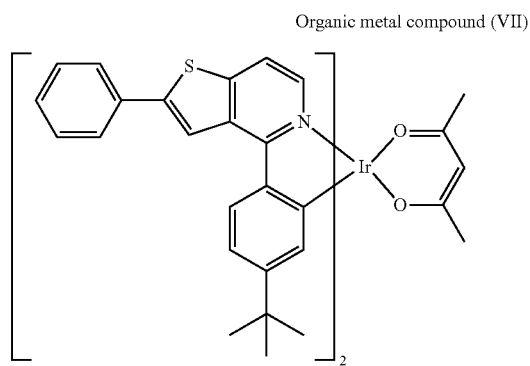

Organic metal compound (VII)

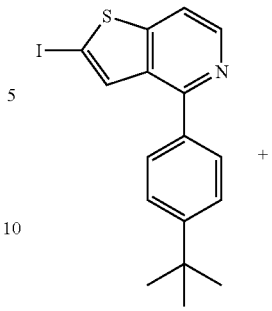

Compound (VI)

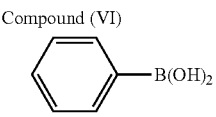

Compound (XVII)

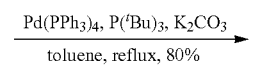
Pd(PPh$_3$)$_4$, P($^t$Bu)$_3$, K$_2$CO$_3$
toluene, reflux, 80%

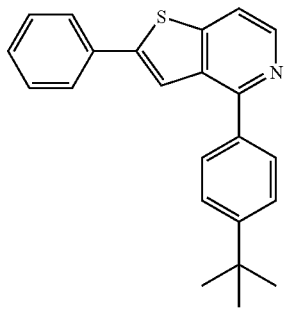

Compound (XVIII)

7.5 g of the compound (VI) (19.0 mmol), 2.8 g of phenylboronic acid (compound (XVII)) (22.9 mmol), tetrakis(triphenyl phosphine) palladium (Pd(PPh$_3$)$_4$) (1.1 g, 0.95 mmol), 18 mL of potassium carbonate (K$_2$CO$_3$) aqueous solution (2M), and 50 mL of toluene were added into a reaction bottle, and the reaction bottle was heated to 110° C. After cooling to room temperature, D.I. water was added into a reaction bottle, and the result was extracted with ethyl acetate as the extraction solvent. After purification by column chromatography (with ethyl acetate and hexane (1:40), a compound (XVIII) with a yield of 74% was obtained. The synthesis pathway of the above reaction was as follows:

The physical measurement of the compound (XVIII) is listed below: $^1$H NMR (CDCl$_3$, 200 MHz) δ 8.51 (d, J=5.6 Hz, 1H), 7.84-7.79 (m, 3H), 7.72-7.68 (m, 3H), 7.57 (d, J=8.4 Hz, 2H), 7.43-7.39 (m, 3H), 1.41 (s, 9H).

Next, 5.0 g of the compound (XVIII) (14.6 mmol), IrCl$_3$·H$_2$O (1.97 g, 6.6 mmol), 15 mL of 2-methoxy ethanol, and 5 mL of water were added into a reaction bottle. After heating to 140° C. and reacting for 24 hours, D.I. water was added into the reaction bottle. After filtration, a compound (XIX) (orange solid) with a yield of 93% was obtained. The synthesis pathway of the above reaction was as follows:

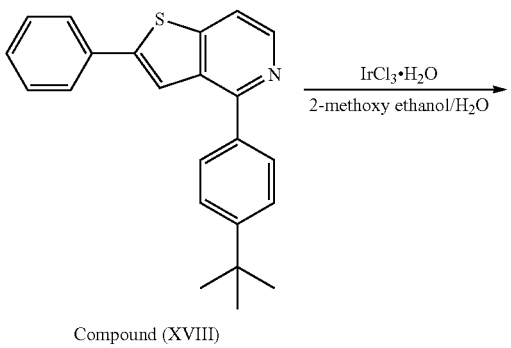

Compound (XVIII)

IrCl$_3$·H$_2$O
2-methoxy ethanol/H$_2$O

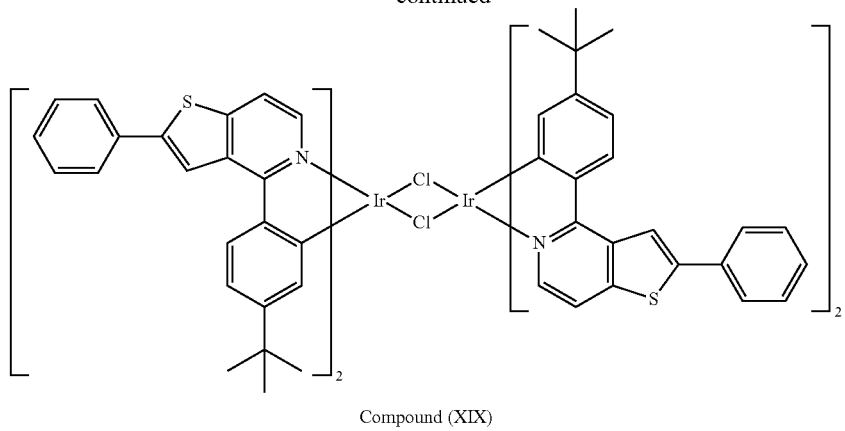

Compound (XIX)

6.2 g of the compound (XIX) (3.40 mmol), 1.7 g of acetyl acetone (13.68 mmol), 1.45 g of Na$_2$CO$_3$ (13.68 mmol), and 2-methoxy ethanol (as solvent) were added into a reaction bottle. The reaction bottle was heated under nitrogen gas to reflux for 12 hours. After cooling to room temperature, five-fold water (by weight) was added into the reaction bottle, and an orange precipitate was obtained. After filtration, the result was extracted with water and dichloromethane. After purification by column chromatography, an organic metal compound (VII) (orange solid) with a yield of 72% was obtained. The synthesis pathway of the above reaction was as follows:

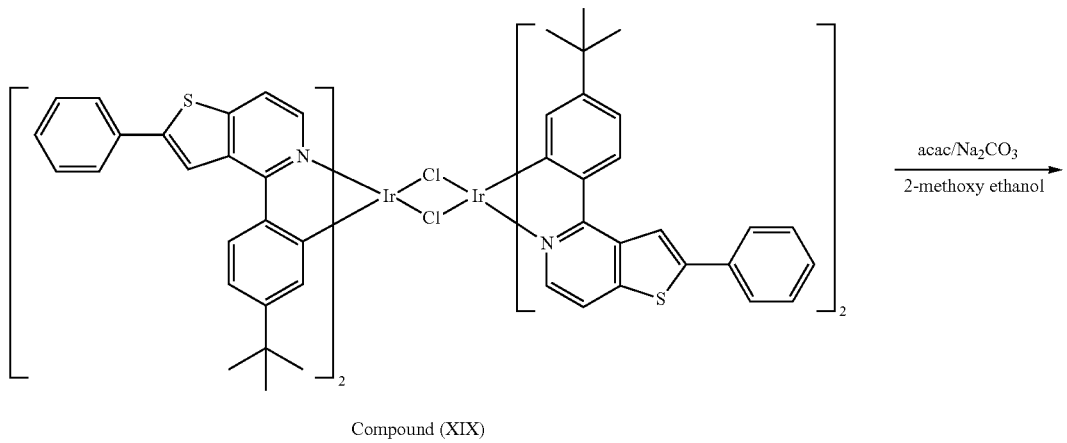

Compound (XIX)

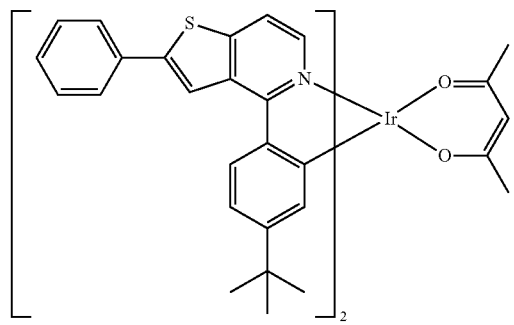

Organic metal compound (VII)

The physical measurement of the organic metal compound (VII) is listed below: $^1$H NMR (CDCl$_3$, 200 MHz) δ 8.46-8.42 (m, 4H), 8.06 (d, J=8.6 Hz, 2H), 7.83 (d, J=8.4 Hz, 4H), 7.61-7.41 (m, 8H), 6.95 (dd, J=8.6, 1.8 Hz, 2H), 6.30 (d, J=2.8 Hz, 2H), 5.24 (s, 1H), 1.80 (s, 6H), 1.00 (s, 18H).

Example 8: Preparation of Organic Metal Compound (VIII)

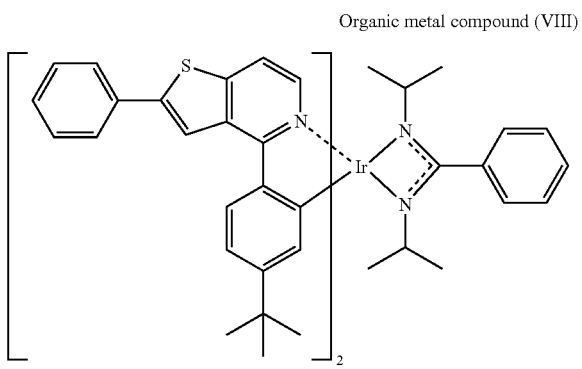

Organic metal compound (VIII)

50 mL of anhydrous tetrahydrofuran (THF), bromobenzene, and 1.43 mL of the compound (X) (13.6 mmol) were added into a reaction bottle. After cooling to −78° C., 8.5 nil of n-butyl lithium (n-BuLi) (13.6 mmol) was dropwisely added into the reaction bottle. After the addition was complete, the mixture was stirred for 30 minutes. Next, 2.1 mL of N,N-diisopropylcarbodiimide (compound XI) (13.6 mmol) was dropwisely added into the reaction bottle at −78° C. After the addition was complete, the mixture was stirred for 30 minutes, obtaining a solution including a compound (XII). The above solution was dropwisely added into a solution including 6.2 g of the compound (XIX) (3.4 mmol) and 70 mL of tetrahydrofuran (THF). After the addition was complete, the bottle was heated to reflux. After reacting for 8 hours, the result was concentrated. After purification by column chromatography with ethyl acetate and hexane (1:4), an organic metal compound (VIII) (red solid) with a yield of 65% was obtained. The synthesis pathway of the above reaction was as follows:

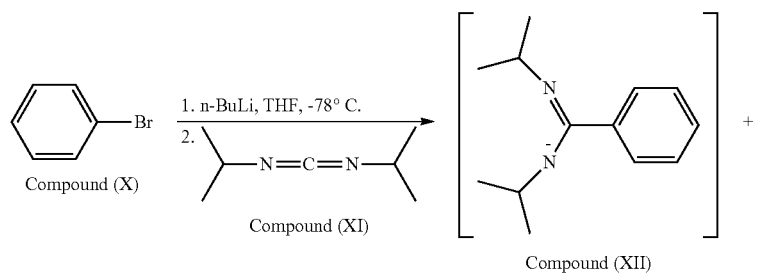

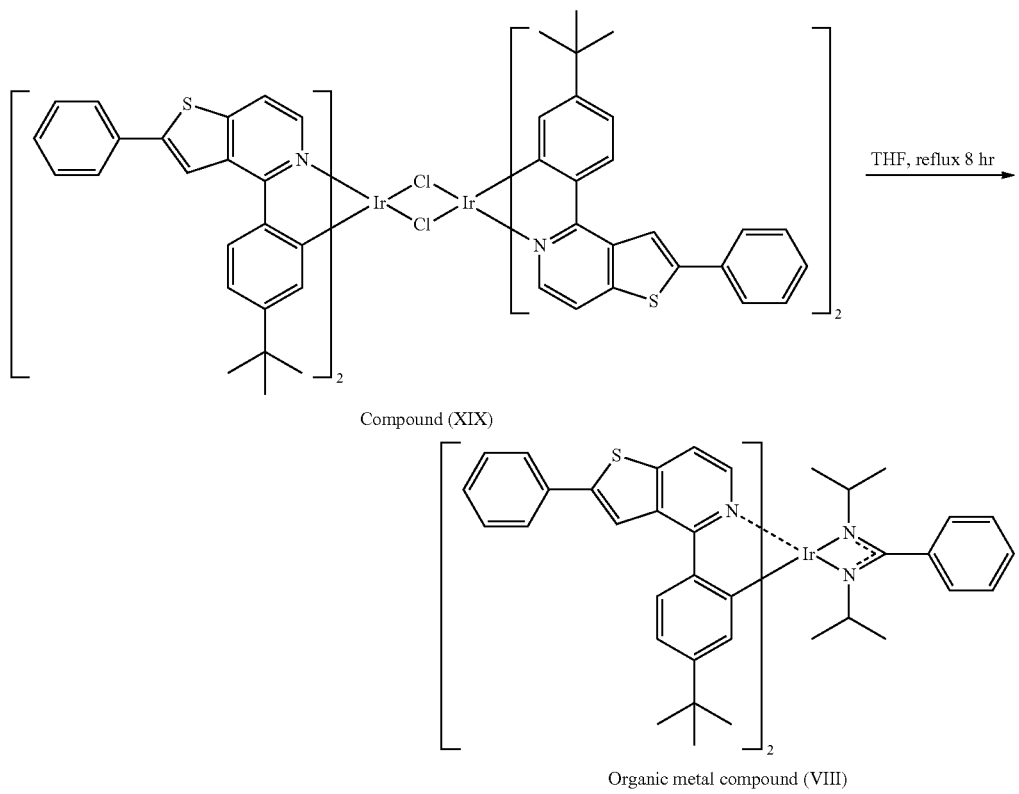

Organic metal compound (VIII)

The physical measurement of the organic metal compound (VIII) is listed below: $^1$H NMR (200 MHz, CDCl$_3$) δ 9.35 (d, J=6.2 Hz, 2H), 8.45 (s, 2H), 8.02 (d, J=8.2 Hz, 2H), 7.74~7.83 (m, 2H), 7.56 (d, J=8.4 Hz, 1H), 7.28~7.43 (m, 4H), 6.96~7.07 (m, 6H), 6.85 (dd, J=8.0, 2.2 Hz, 2H), 6.38 (d, J=1.8 Hz, 2H), 0.97 (s, 18H), 0.67 (d, J=6.2 Hz, 6H), −0.06 (d, J=6.4 Hz, 6H).

Example 9: Preparation of Organic Metal Compound (IX)

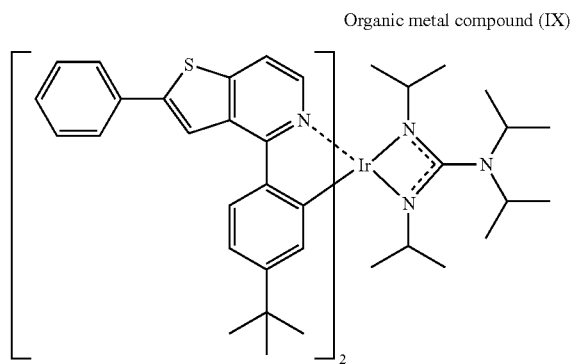

Organic metal compound (IX)

50 mL of anhydrous tetrahydrofuran (THF) and 1.95 mL of N,N-diisopropylcarbodiimide (compound XI) (12.51 mmol) were added into a reaction bottle. After cooling to −78° C., 9.4 mL of lithium diisopropylamide (LDA) (18.76 mmol) was dropwisely added into the reaction bottle. After the addition was complete, the mixture was mixed for 1 hour, obtaining a solution including the compound (XIII). The above solution was dropwisely added into a solution including 6.15 g of the compound (XIX) (3.13 mmol) and 70 mL of tetrahydrofuran (THF). After the addition was complete, the bottle was heated to reflux. After reacting for 8 hours, the result was concentrated. After purification by column chromatography with ethyl acetate and hexane (1:6), an organic metal compound (IX) (brown solid) with a yield of 37% was obtained. The synthesis pathway of the above reaction was as follows:

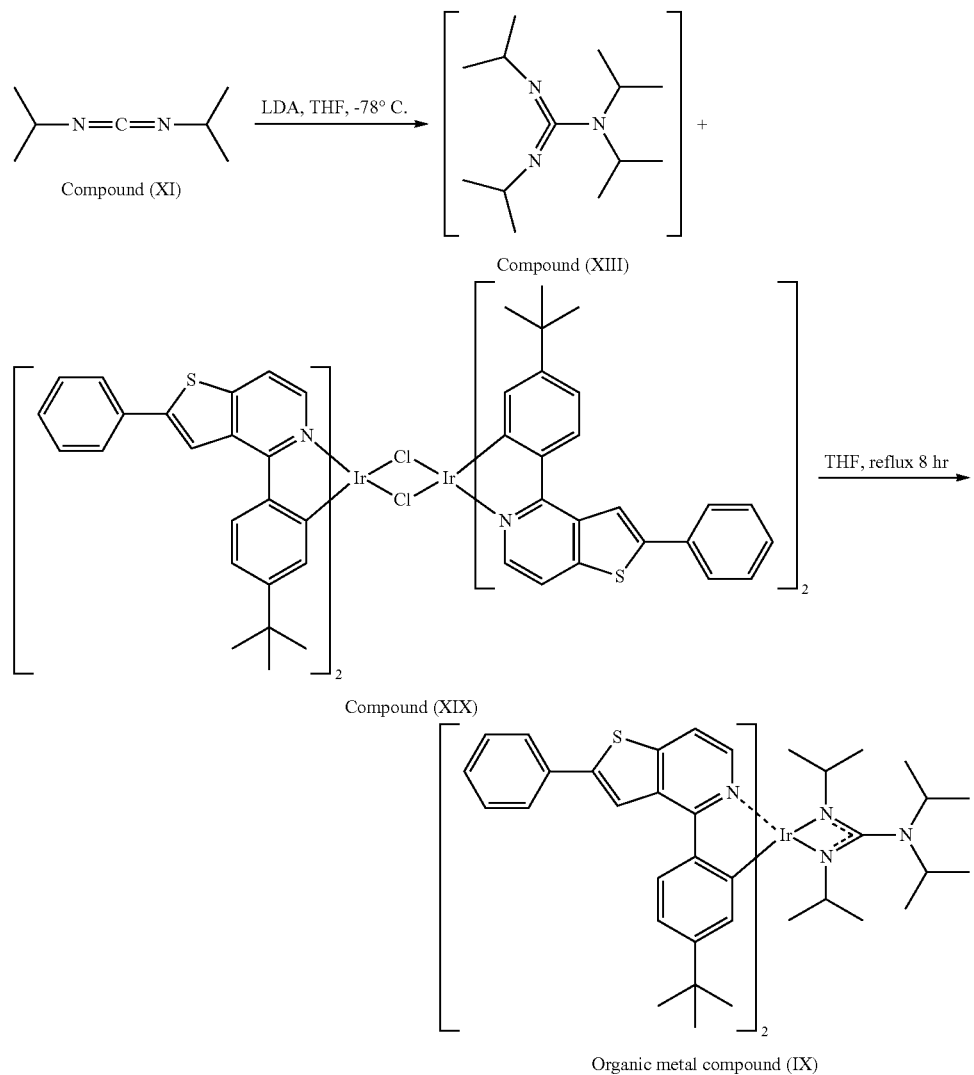

The physical measurement of the organic metal compound (IX) is listed below: $^1$H NMR (200 MHz, CDCl$_3$) δ 9.22 (d, J=6.2 Hz, 2H), 8.53 (s, 2H), 7.98 (d, J=8.4 Hz, 2H), 7.69~7.78 (m, 2H), 7.60 (d, J=6.2 Hz, 2H), 6.97~7.08 (m, 4H), 6.85 (dd, J=8.0, 1.8 Hz, 2H), 6.32 (s, 2H), 3.83 (m, 2H), 3.52 (m, 2H), 1.24 (m, 12H), 0.96 (s, 18H), 0.84 (d, J=6.2 Hz, 6H), −0.02 (d, J=6.2 Hz, 6H).

Example 10

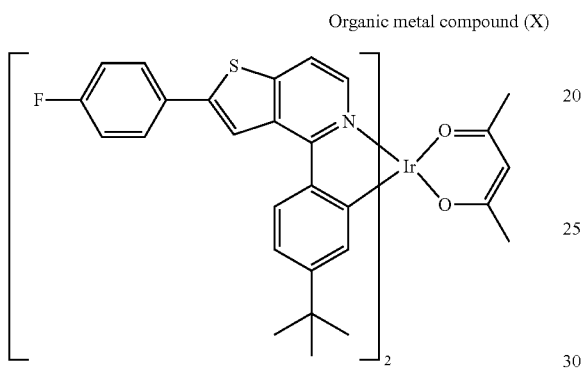

Organic metal compound (X)

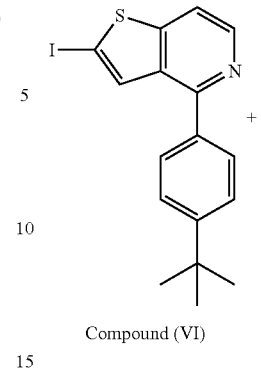

Compound (VI)

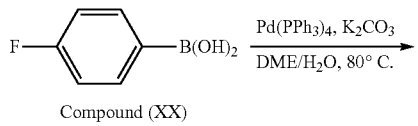

Compound (XX)

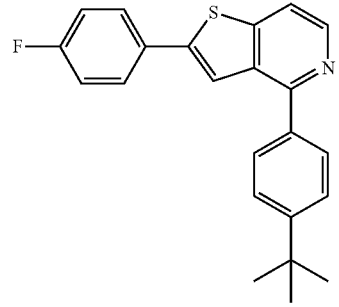

Compound (XXI)

7.86 g of the compound (VI) (20 mmol), 5.6 g of 4-fluorophenylboronic acid (40 mmol), 0.92 g of tetrakis (triphenyl phosphine) palladium (Pd(PPh$_3$)$_4$) (0.8 mmol), 5.53 g of potassium carbonate (K$_2$CO$_3$) (40 mmol), 26.7 mL of 1,2-dimethoxyethane (DME), and 13.3 mL of water were added into a reaction bottle, and the reaction bottle was heated to 80° C. After cooling, water was added into the reaction bottle, and the result was extracted with ethyl acetate as the extraction solvent. After purification by column chromatography (with ethyl acetate and hexane (1:20), a compound (XXI) with a yield of 80% was obtained. The synthesis pathway of the above reaction was as follows:

5.82 g of the compound (XXI) (16.12 mmol, 2.2 eq.), IrCl$_3$.H$_2$O (2.18 g, 7.33 mmol), 15 mL of 2-methoxy ethanol, and 5 mL of water were added into a reaction bottle. The reaction bottle was heated to 140° C. After reacting for 24 hours, D.I. water was added into the reaction bottle. After filtration, a compound (XXII) (orange solid) with a yield of 81% was obtained. The synthesis pathway of the above reaction was as follows:

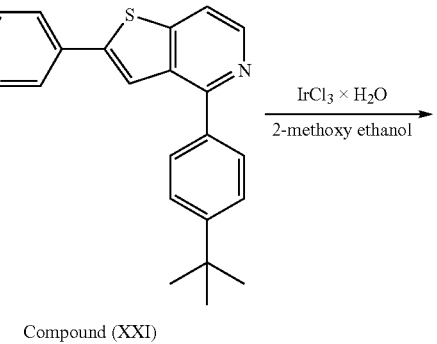

Compound (XXI)

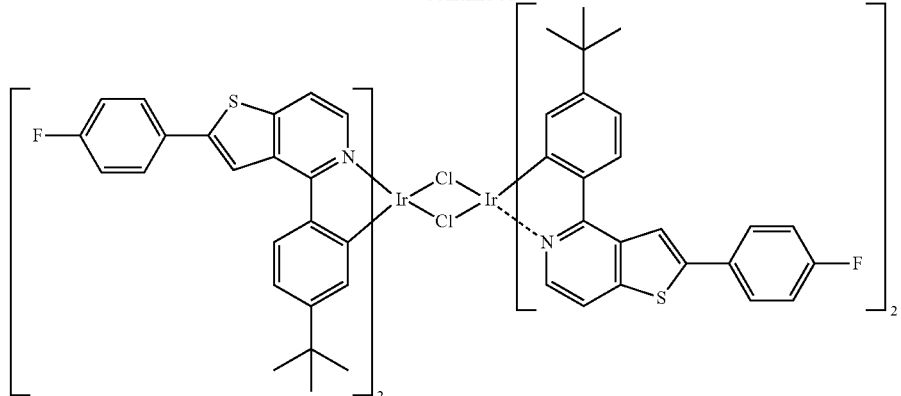

Compound (XXII)

5.64 g of the compound (XXII) (2.98 mmol), 1.2 g of 2,4-pentanedione (11.91 mmol), 1.26 g of sodium carbonate (11.91 mmol), and 30 mL of 2-methoxyethanol were added into a reaction bottle. The reaction bottle was heated to 140° C. After reacting for 24 hours, the reaction bottle was cooled to room temperature, and D.I. water (50 mL) was added into the reaction bottle. After purification by column chromatography with dichloromethane and n-hexane (1:1), an organic metal compound (X) (orange solid) with a yield of 37% was obtained. The synthesis pathway of the above reaction was as follows:

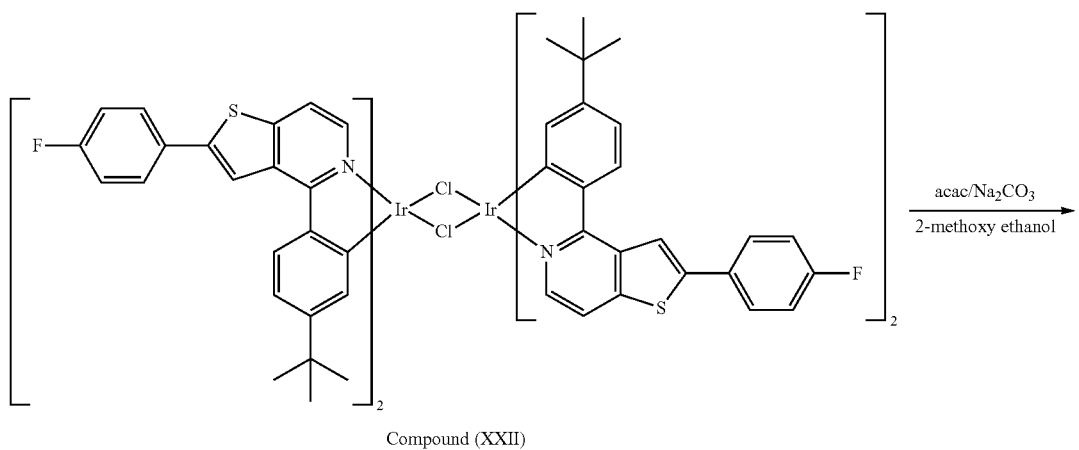

Compound (XXII)

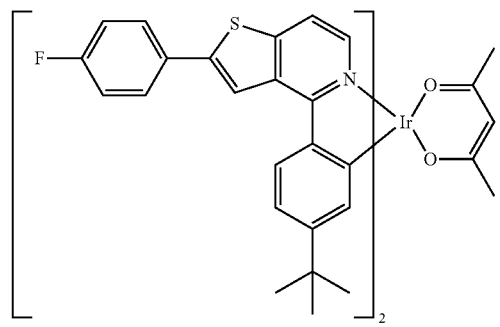

Organic metal compound (X)

The physical measurement of the organic metal compound (X) is listed below: $^1$H NMR (200 MHz, CDCl$_3$) δ 8.44 (d, J=6.6 Hz, 2H), 8.38 (s, 2H), 8.02 (d, J=8.4 Hz, 2H), 7.74~7.81 (m, 4H), 7.58 (d, J=6.4 Hz, 2H), 7.19 (t, J=8.4 Hz, 4H), 6.30 (d, J=2.2 Hz, 2H), 5.23 (s, 1H), 1.80 (s, 6H), 0.99 (s, 18H).

Example 11 organic metal compound (XI)

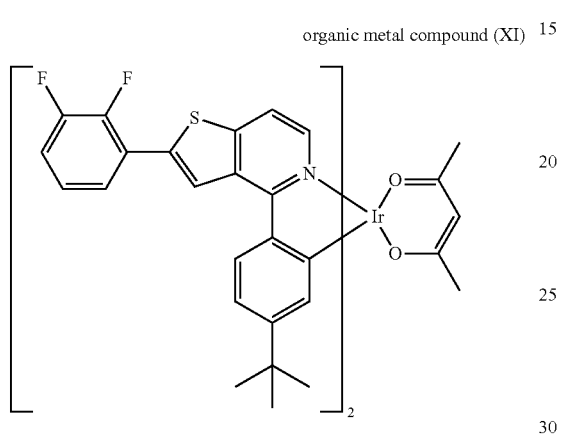

7.86 g of compound (VI) (20 mmol), 2,3-difluorophenylboronic acid (6.32 g, 40 mmol), 0.92 g of tetrakis(triphenyl phosphine) palladium (Pd(PPh$_3$)$_4$) (0.8 mmol), 5.53 g of potassium carbonate (K$_2$CO$_3$) (40 mmol), 26.7 mL of 1,2-dimethoxyethane (DME), and 13.3 mL of water were added into a reaction bottle, and the reaction bottle was heated to 80° C., After cooling, the result was extracted with ethyl acetate as the extraction solvent. After purification by column chromatography with ethyl acetate and hexane (1:40), a compound (XXIV) with a yield of 40% was obtained. The synthesis pathway of the above reaction was as follows:

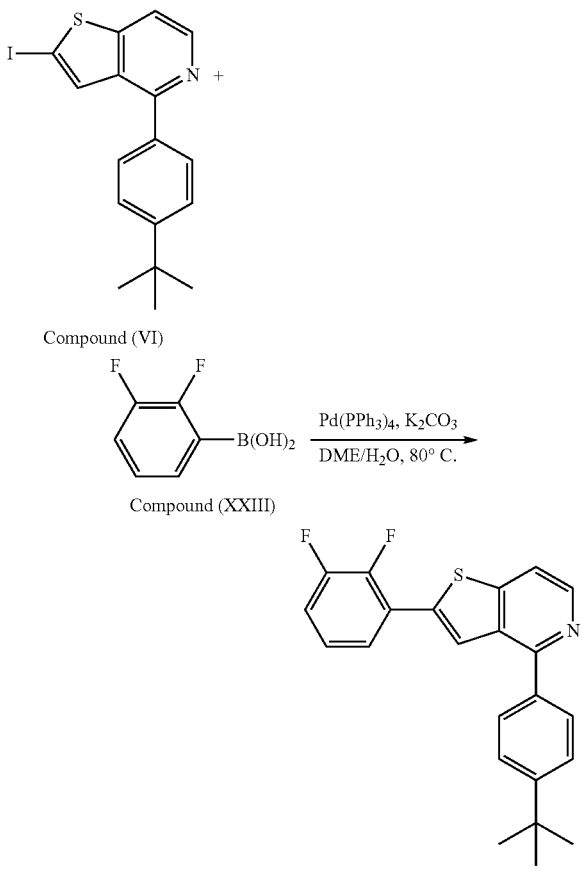

3.03 g of the compound (XXIV) (7.99 mmol, 2.2 eq.), 1.08 g of IrCl$_3$.H$_2$O (3.63 mmol), 15 mL of 2-methoxy ethanol, and 5 mL of water were added into a reaction bottle, and the reaction bottle was heated to 140° C. After reacting for 24 hours, D.I. water was added into the reaction bottle. After filtration, a compound (XXV) (orange solid) with a yield of 94% was obtained. The synthesis pathway of the above reaction was as follows:

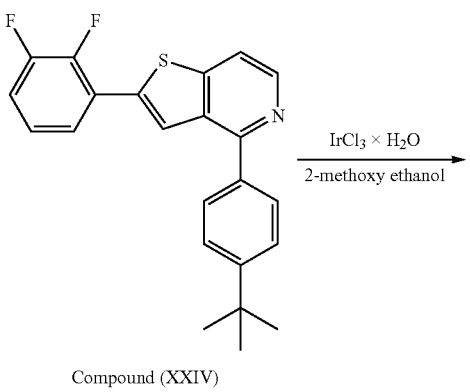

Compound (XXIV)

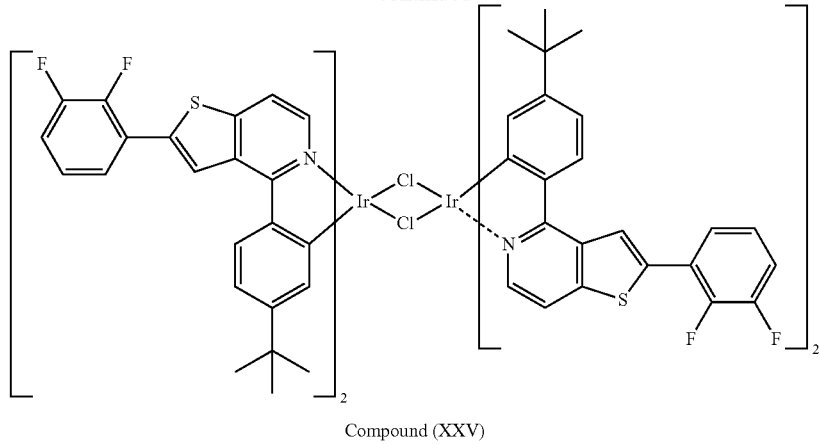

Compound (XXV)

3.39 g of the compound (XXV) (1.72 mmol), 0.69 g of 2,4-pentanedione (6.89 mmol), 0.73 g of sodium carbonate (6.89 mmol), and 20 mL of 2-methoxyethanol were added into a reaction bottle, and the reaction bottle was heated to 140° C. After reacting for 24 hours, the reaction bottle was cooled to room temperature and D.I. water (50 mL) was added into the reaction bottle. After purification by column chromatography with dichloromethane and n-hexane (1:3), an organic metal compound (XI) (orange solid) with a yield of 83% was obtained. The synthesis pathway of the above reaction was as follows:

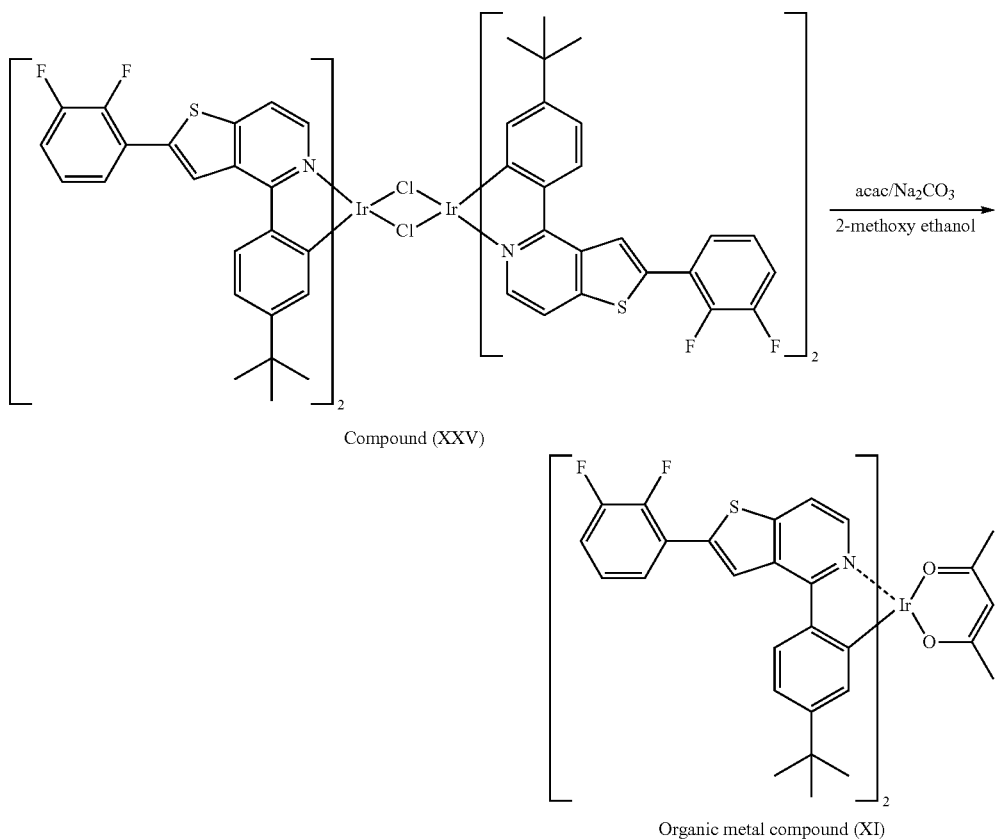

The physical measurement of the organic metal compound (XI) is listed below: $^1$H NMR (200 MHz, CDCl$_3$) δ 8.67 (s, 2H), 8.46 (d, J=6.2 Hz, 2H), 8.02 (d, J=8.6 Hz, 2H), 7.61 (d, J=6.2 Hz, 4H), 7.21 (d, J=6.4 Hz, 2H), 6.94 (dd, J=8.4, 2.2 Hz, 2H), 6.30 (d, J=1.8 Hz, 2H), 5.23 (s, 1H), 1.80 (s, 6H), 0.89 (s, 18H).

Example 12

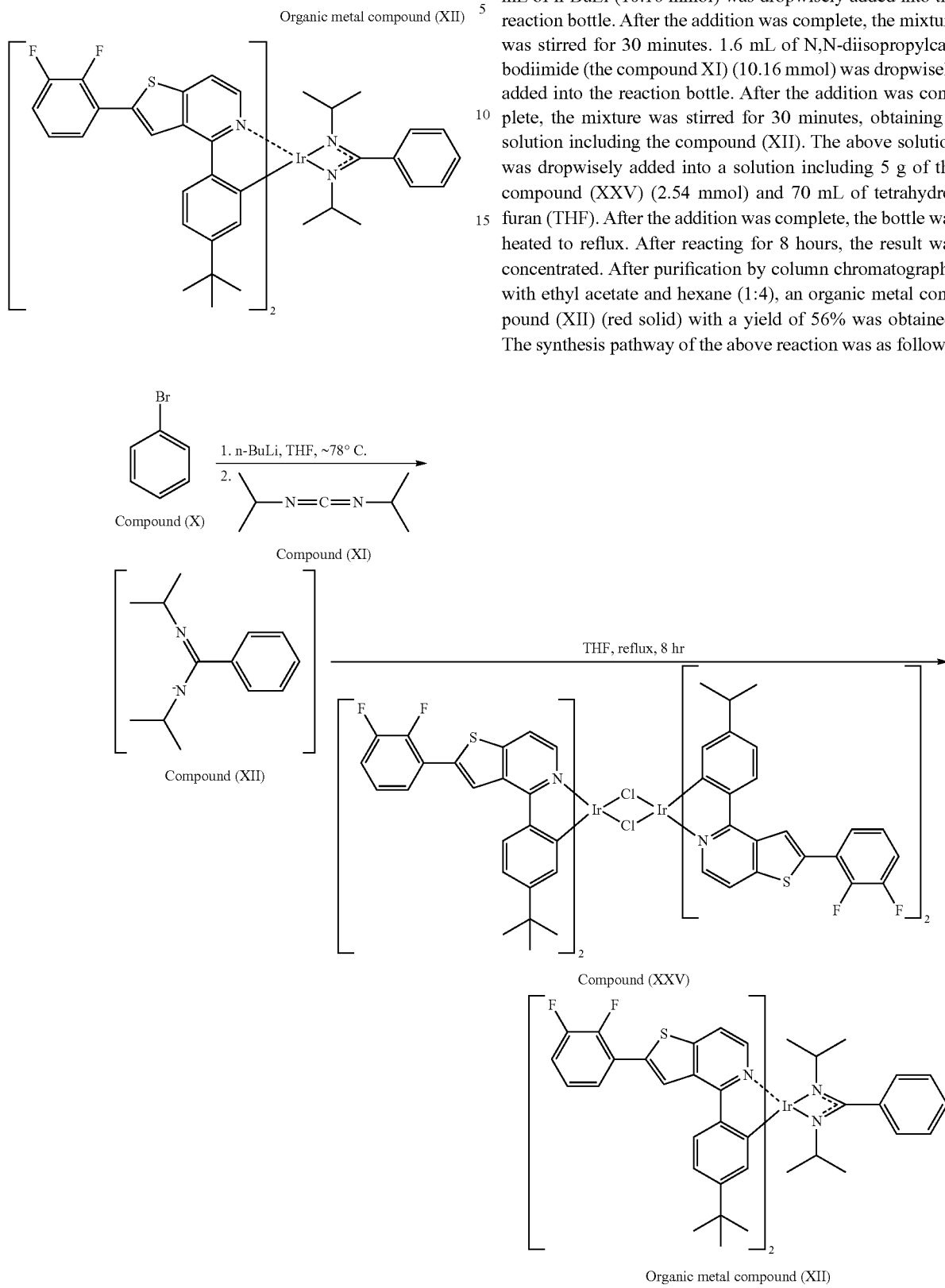

50 mL of anhydrous tetrahydrofuran (THF), 1.1 mL of bromobenzene (the compound (X)) (10.16 mmol) were added into a reaction bottle. After cooling to −78° C., 6.35 mL of n-BuLi (10.16 mmol) was dropwisely added into the reaction bottle. After the addition was complete, the mixture was stirred for 30 minutes. 1.6 mL of N,N-diisopropylcarbodiimide (the compound XI) (10.16 mmol) was dropwisely added into the reaction bottle. After the addition was complete, the mixture was stirred for 30 minutes, obtaining a solution including the compound (XII). The above solution was dropwisely added into a solution including 5 g of the compound (XXV) (2.54 mmol) and 70 mL of tetrahydrofuran (THF). After the addition was complete, the bottle was heated to reflux. After reacting for 8 hours, the result was concentrated. After purification by column chromatography with ethyl acetate and hexane (1:4), an organic metal compound (XII) (red solid) with a yield of 56% was obtained. The synthesis pathway of the above reaction was as follows:

The physical measurement of the organic metal compound (XII) is listed below: $^1$H NMR (200 MHz, CDCl$_3$) δ 9.42 (d, J=6.6 Hz, 2H), 8.67 (s, 2H), 8.02 (d, J=8.6 Hz, 2H), 7.75 (d, J=6.2 Hz, 2H), 7.54~7.58 (m, 2H), 7.30~7.45 (m, 6H), 6.89 (dd, J=8.4, 2.2 Hz, 2H), 6.39 (d, J=2.2 Hz, 2H), 3.28 (m, 1H), 0.99 (s, 18H), 0.69 (d, J=6.2 Hz, 6H), −0.04 (d, J=6.4 Hz, 6H).

Example 13

3.0 g of the compound (IX) (1.56 mmol), 0.768 g of picolinic acid (6.24 mmol), 0.66 g of sodium carbonate (6.24 mmol), and 20 mL of 2-methoxyethanol were added into a reaction bottle, and the reaction was heated to 140° C. After reacting for 24 hours, the reaction bottle was cooled to room temperature, and D.I. water (50 mL) was added into the reaction bottle. After purification by column chromatography with dichloromethane/ethyl acetate (9:1), an organic metal compound (XIII) (orange solid) with a yield of 42% was obtained. The synthesis pathway of the above reaction was as follows:

organic metal compound (XIII)

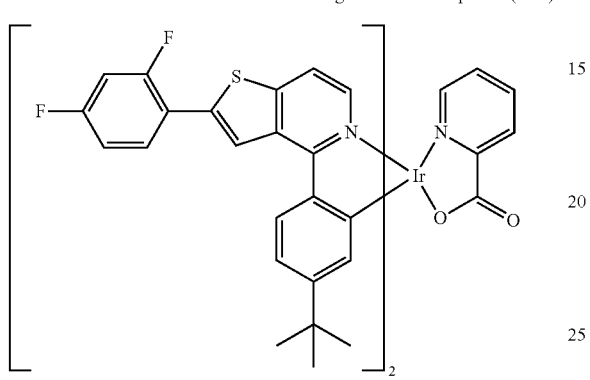

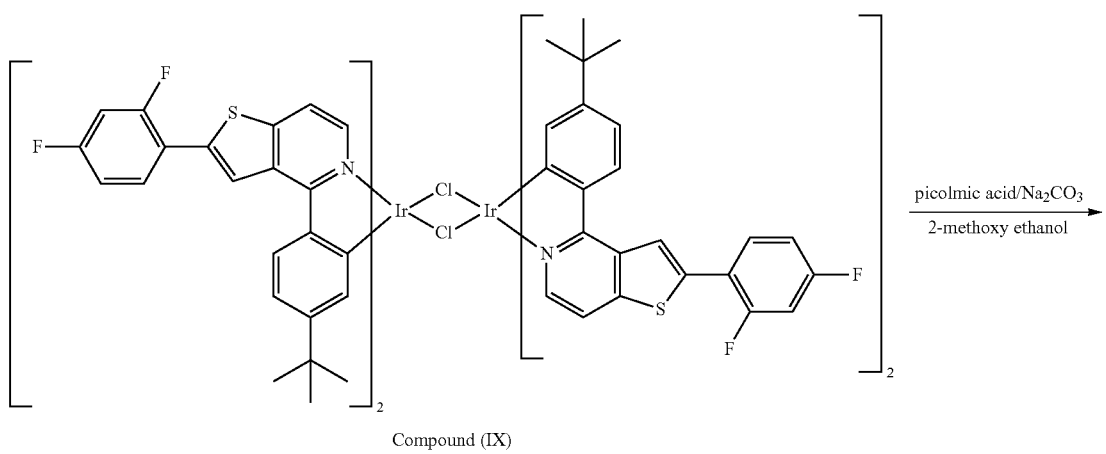

Compound (IX)

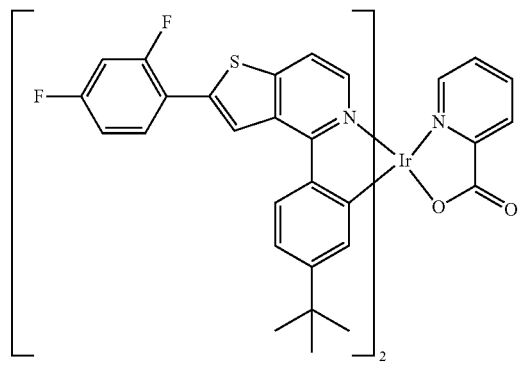

Organic metal compound (XIII)

The physical measurement of the organic metal compound (XIII) is listed below: $^1$H NMR (200 MHz, CDCl$_3$) δ 8.74 (d, J=6.6 Hz, 1H), 8.56 (d, J=5.0 Hz, 2H), 8.35 (d, J=8.6 Hz, 1H), 8.03~8.09 (m, 2H), 7.87 (t, J=6.2 Hz, 1H), 7.72~7.76 (m, 2H), 7.62 (t, J=6.6 Hz, 2H), 7.33~7.42 (m, 3H), 6.96~7.08 (m, 5H), 6.48 (d, J=1.8 Hz, 1H), 6.19 (d, J=1.8 Hz, 1H), 1.05 (s, 9H), 0.88 (s, 9H).

Example 14

Organic metal compound (XIV)

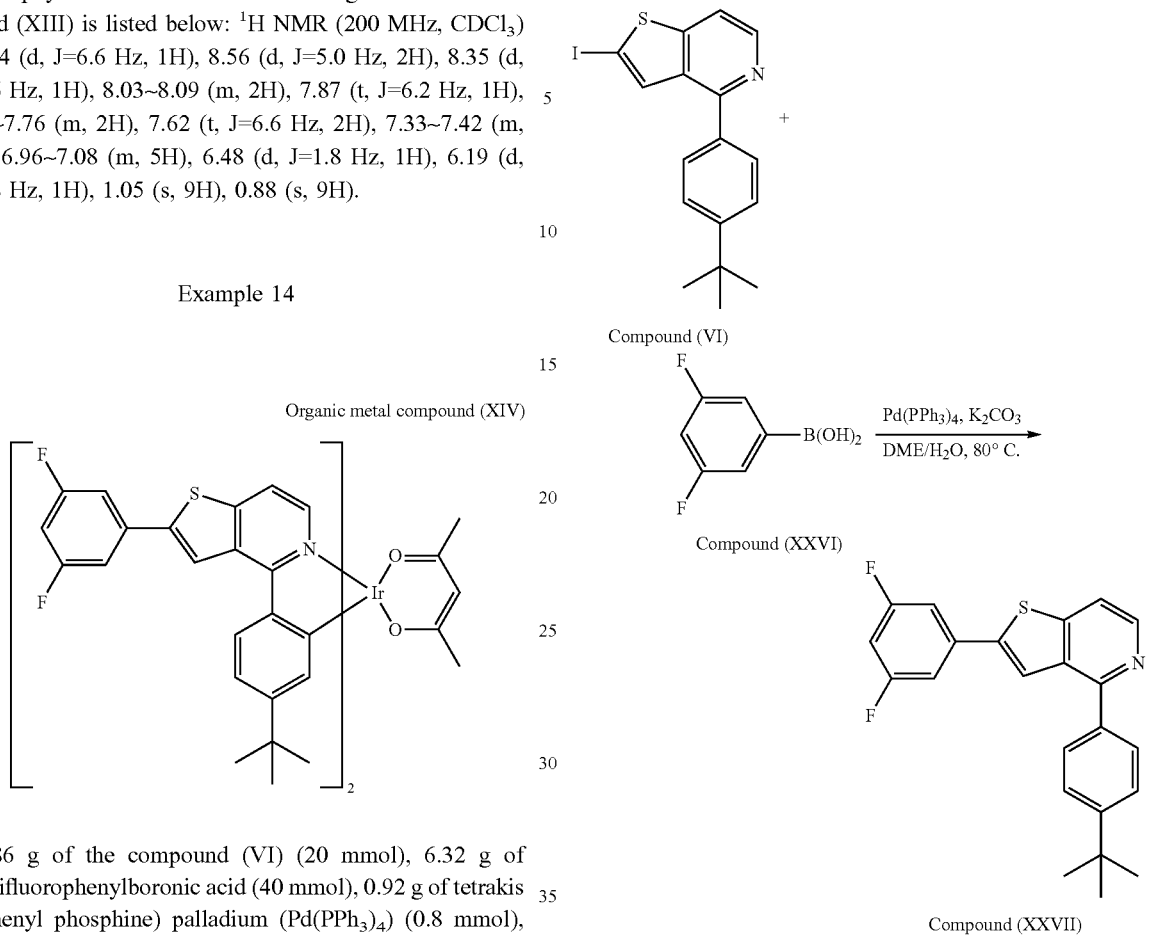

7.86 g of the compound (VI) (20 mmol), 6.32 g of 3,5-difluorophenylboronic acid (40 mmol), 0.92 g of tetrakis (triphenyl phosphine) palladium (Pd(PPh$_3$)$_4$) (0.8 mmol), 5.53 g of potassium carbonate (K$_2$CO$_3$) (40 mmol), 26.7 mL of 1,2-dimethoxyethane (DME) and 13.3 mL of water were added into a reaction bottle, and the reaction bottle was heated to 80° C. After cooling, the result was extracted with ethyl acetate as the extraction solvent. After purification by column chromatography (with ethyl acetate and hexane (1:40), a compound (XXVII) with a yield of 40% was obtained. The synthesis pathway of the above reaction was as follows:

3.03 g of the compound (XXVII) (7.99 mmol, 2.2 eq.), 1.08 g of IrCl$_3$.H$_2$O (3.63 mmol), 15 mL of 2-methoxy ethanol and 5 mL of water were added into a reaction bottle were added into a reaction bottle, and the reaction bottle was heated to 140° C. After reacting for 24 hours, D.I. water was added into the reaction bottle. After filtration, a compound (XXVIII) (orange solid) with a yield of 94% was obtained. The synthesis pathway of the above reaction was as follows:

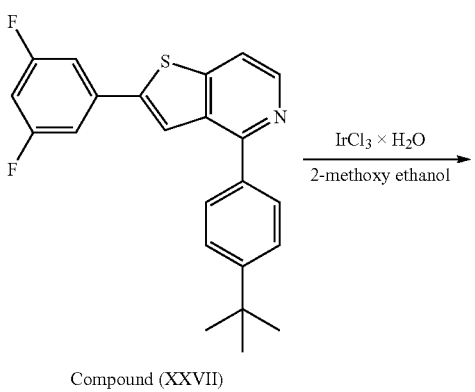

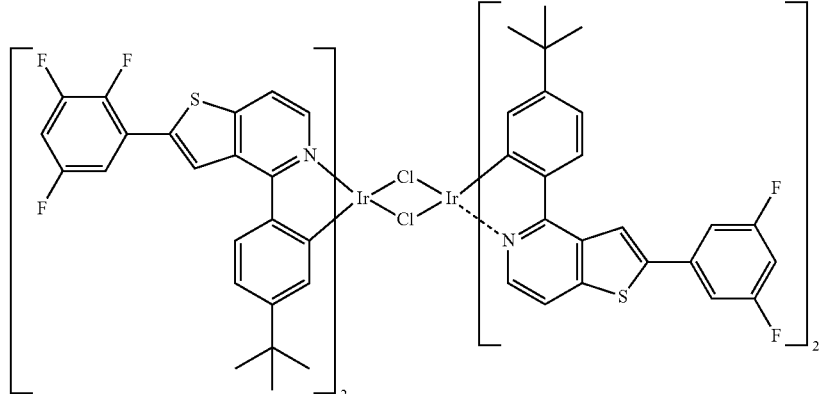

Compound (XXVIII)

3.39 g of the compound (XXVIII) (1.72 mmol), 0.69 g of 2,4-pentanedione (6.89 mmol), 0.73 g of sodium carbonate (6.89 mmol) and 20 mL of 2-methoxyethanol were added into a reaction bottle, and the reaction bottle was heated to 140° C. After reacting for 24 hours, the reaction bottle was cooled to room temperature, and D.I. water (50 mL) was added into the reaction bottle. After purification by column chromatography with dichloromethane and n-hexane (1:3), an organic metal compound (XIV) (orange solid) with a yield of 83% was obtained. The synthesis pathway of the above reaction was as follows:

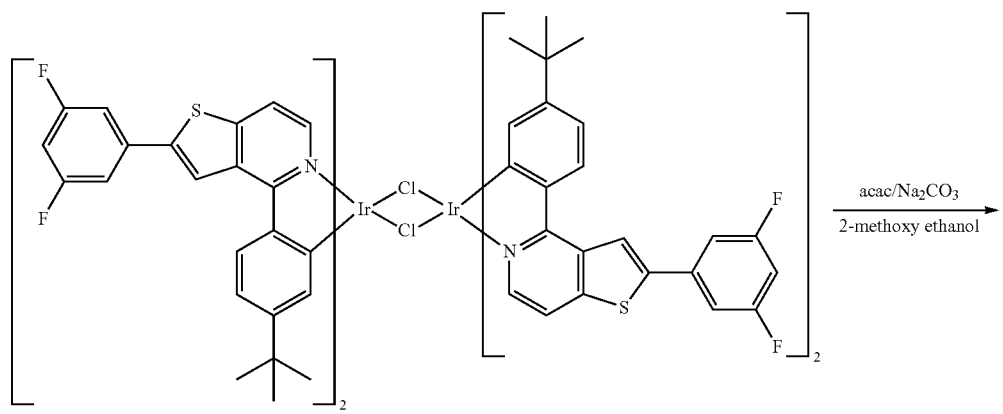

Compound (XXVIII)

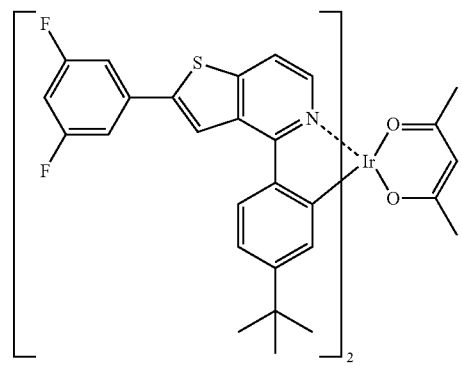

Organic metal compound (XIV)

The physical measurement of the organic metal compound (XIV) is listed below: $^1$H NMR (200 MHz, CDCl$_3$) δ8.55 (d, J=5.4 Hz, 2H), 8.47 (s, 2H), 8.02 (d, J=8.4 Hz, 2H), 7.71~7.77 (m, 4H), 7.20~7.34 (m, 2H), 6.98 (d, J=6.2 Hz, 2H), 6.29 (s, 2H), 5.25 (s, 1H), 1.81 (s, 6H), 1.01 (s, 18H).

Example 15

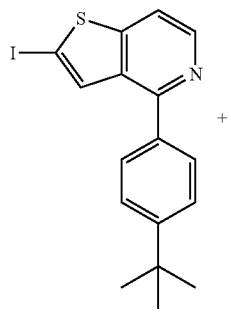

Compound (VI)

Organic metal compound (XV)

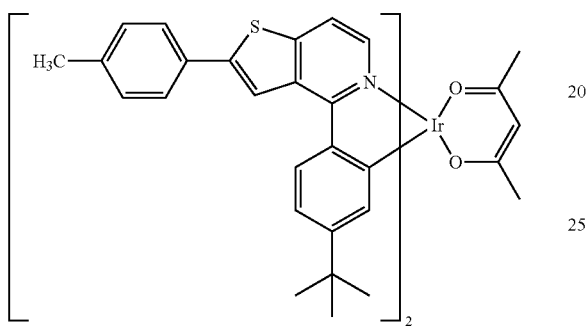

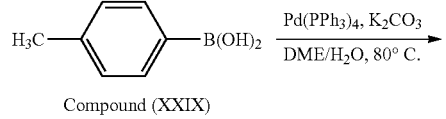

Compound (XXIX)

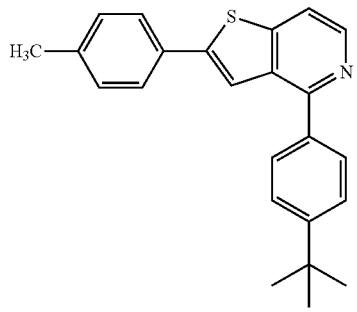

Compound (XXX)

7.83 g the compound (VI) (19.9 mmol), 5.42 g of 4-methyl phenylboronic acid (39.83 mmol), 0.92 g of tetrakis(triphenyl phosphine) palladium (Pd(PPh$_3$)$_4$) (0.7966 mmol), 5.51 g of potassium carbonate (K$_2$CO$_3$) (39.83 mmol), 26.7 mL of 1,2-dimethoxyethane (DME), and 13.3 mL of water were added into a reaction bottle, and the reaction bottle was heated to 80° C. After cooling, the result was extracted with ethyl acetate as the extraction solvent. After purification by column chromatography (with ethyl acetate and hexane (1:20), a compound (XXX) with a yield of 95% was obtained. The synthesis pathway of the above reaction was as follows:

5 g of the compound (XXX) (14 mmol, 2.2 eq.), IrCl$_3$.H$_2$O (1.9 g, 6.37 mmol), 15 mL 2-methoxy ethanol, and 5 mL of water were added into a reaction bottle, and the reaction bottle was heated to 140° C. After reacting for 24 hours, D.I. water was added into the reaction bottle. After filtration, a compound (XXXI) (orange solid) with a yield of 95% was obtained. The synthesis pathway of the above reaction was as follows:

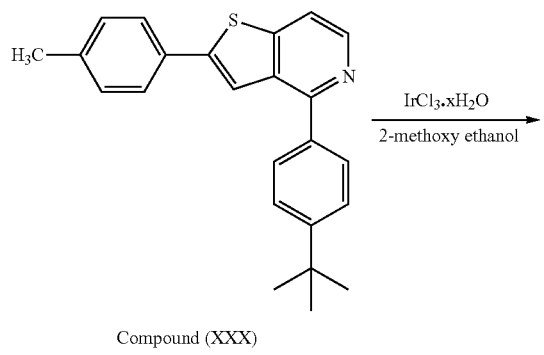

Compound (XXX)

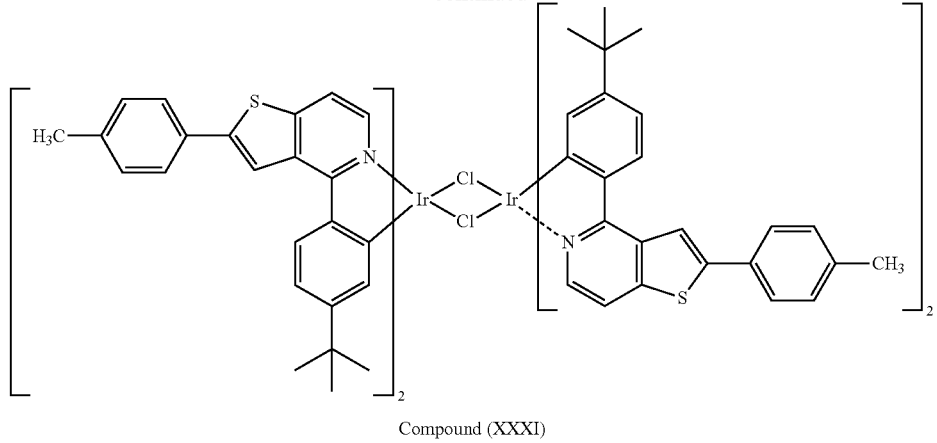

Compound (XXXI)

5.77 g of the compound (XXXI) (3.045 mmol) 1.22 g of 2,4-pentanedione (12.18 mmol), 1.29 g of sodium carbonate (12.18 mmol) and 30 mL of 2-methoxyethanol were added into a reaction bottle, and the reaction bottle was heated to 140° C. After reacting for 24 hours, the reaction bottle was cooled to room temperature and D.I. water (50 mL) was added into the reaction bottle. After purification by column chromatography with dichloromethane and n-hexane (1:1), an organic metal compound (XV) (orange solid) with a yield of 56% was obtained. The synthesis pathway of the above reaction was as follows:

The physical measurement of the organic metal compound (XV) is listed below: $^1$H NMR (200 MHz, CDCl$_3$) δ 8.42 (d, J=6.2 Hz, 4H), 8.04 (d, J=8.4 Hz, 2H), 7.70 (d, J=8.0 Hz, 4H), 7.58 (d, J=6.6 Hz, 2H), 7.27~7.33 (m, 4H), 6.93 (dd, J=8.0, 1.8 Hz, 2H), 6.29 (d, J=1.8 Hz, 2H), 5.30 (s, 1H), 2.45 (s, 6H), 1.80 (s, 6H), 0.90 (s, 18H).

Example 16: Fabrication of the Organic Light-Emitting Device (1) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

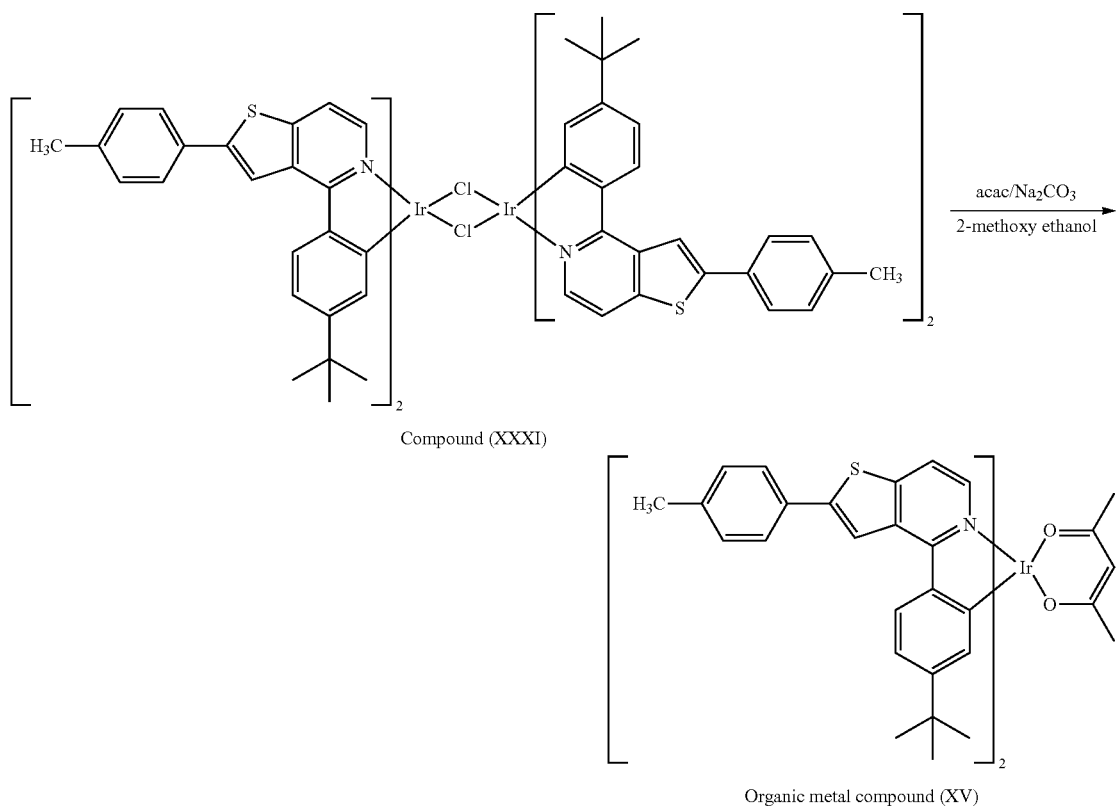

Compound (XXXI)

Organic metal compound (XV)

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, TAPC (di-[4-(N,N-ditolyl-amino)-phenyl]cyclohexane, with a thickness of 35 nm), TCTA (4,4',4"-tris (carbazol-9-yl)triphenylamine) doped with the organic metal compound (I) (the weight ratio between TCTA and the organic metal compound (I) was 100:3, with a thickness of 10 nm), TmPyPB (1,3,5-tri[(3-pyridyl)-phen-3-yl]benzene, with a thickness of 42 nm), LiF (with a thickness of 0.5 nm), and Al (with a thickness of 120 nm) were subsequently formed on the PEDO:PSS film at 10-6 Pa, obtaining the organic light-emitting device (1) after encapsulation. The materials and layers formed therefrom are described in the following:

ITO (150 nm)/PEDOT:PSS (45 nm)/TAPC (35 nm)/TCTA: organic metal compound (I) (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and (C.I.E coordinates (x, y)) of the organic light-emitting device (1) were measured. The results are shown in Table 2.

Example 17: Fabrication of the Organic Light-Emitting Device (2) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, TAPC (di-[4-(N,N-ditolyl-amino)-phenyl]cyclohexane, with a thickness of 35 nm), TCTA (4,4',4"-tris (carbazol-9-yl)triphenylamine) doped with the organic metal compound (II) (the weight ratio between TCTA and the organic metal compound (II) was 100:3, with a thickness of 10 nm), TmPyPB (1,3,5-tri[(3-pyridyl)-phen-3-yl]benzene, with a thickness of 42 nm), LiF (with a thickness of 0.5 nm), and Al (with a thickness of 120 nm) were subsequently formed on the PEDO:PSS film at 10-6 Pa, obtaining the organic light-emitting device (2) after encapsulation. The materials and layers formed therefrom are described in the following:

ITO (150 nm)/PEDOT:PSS (45 nm)/TAPC (35 nm)/TCTA: organic metal compound (II) (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (2) were measured. The results are shown in Table 2.

Example 18: Fabrication of the Organic Light-Emitting Device (3) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, TAPC (di-[4-(N,N-ditolyl-amino)-phenyl]cyclohexane, with a thickness of 35 nm), TCTA (4,4',4"-tris (carbazol-9-yl)triphenylamine) doped with the organic metal compound (III) (the weight ratio between TCTA and the organic metal compound (III) was 100:3, with a thickness of 10 nm), TmPyPB (1,3,5-tri[(3-pyridyl)-phen-3-yl] benzene, with a thickness of 42 nm), LiF (with a thickness of 0.5 nm), and Al (with a thickness of 120 nm) were subsequently formed on the PEDO:PSS film at 10-6 Pa, obtaining the organic light-emitting device (3) after encapsulation. The materials and layers formed therefrom are described in the following:

ITO (150 nm)/PEDOT:PSS (45 nm)/TAPC (35 nm)/TCTA: organic metal compound (III) (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (3) were measured. The results are shown in Table 2.

Example 19: Fabrication of the Organic Light-Emitting Device (4) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next. TAPC (di-[4-(N,N-ditolyl-amino)-phenyl]cyclohexane, with a thickness of 35 nm), TCTA (4,4',4"-tris (carbazol-9-yl)triphenylamine) doped with the organic metal compound (IV) (the weight ratio between TCTA and the organic metal compound (IV) was 100:3, with a thickness of 10 nm), TmPyPB (1,3,5-tri[(3-pyridyl)-phen-3-yl] benzene, with a thickness of 42 nm), LiF (with a thickness of 0.5 nm), and Al (with a thickness of 120 nm) were subsequently formed on the PEDO:PSS film at 10-6 Pa, obtaining the organic light-emitting device (4) after encapsulation. The materials and layers formed therefrom are described in the following:

ITO (150 nm)/PEDOT:PSS (45 nm)/TAPC (35 nm)/TCTA: organic metal compound (IV) (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (4) were measured. The results are shown in Table 2.

Comparative Example 1: Fabrication of the Organic Light-Emitting Device (5) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a ITV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, TAPC (di-[4-(N,N-ditolyl-amino)-phenyl]cyclohexane, with a thickness of 35 nm), TCTA (4,4',4''-tris (cartazol-9-yl)triphenylamine) doped with an organic metal compound (PO-08, having a structure of

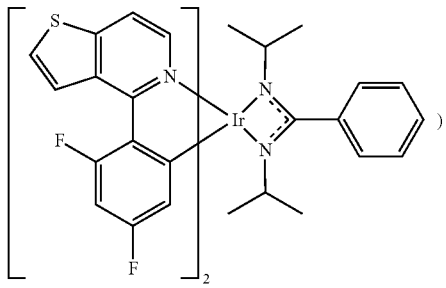

(the weight ratio between TCTA and the organic metal compound PO-08 was 100:3, with a thickness of 10 nm), TmPyPB (1,3,5-tri[(3-pyridyl)-phen-3-yl]benzene, with a thickness of 42 nm), LiF (with a thickness of 0.5 nm), and Al (with a thickness of 120 nm) were subsequently formed on the PEDOT:PSS film at 10-6 Pa, obtaining the organic light-emitting device (5) after encapsulation. The materials and layers formed therefrom are described in the following:
ITO (150 nm)/PEDOT:PSS (45 nm)/TAPC (35 nm)/TCTA: PO-08 (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (5) were measured. The results are shown in Table 2.

Comparative Example 2: Fabrication of the Organic Light-Emitting Device (6) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a ITV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, TAPC (di-[4-(N,N-ditolyl-amino)-phenyl]cyclohexane, with a thickness of 35 nm), TCTA (4,4',4''-tris (carbazol-9-yl)triphenylamine) doped with an organic metal compound Ir(phq)$_2$acac (bis(2-phenylquinoline)(acetylacetonate)iridium(III))) (the weight ratio between TCTA and Ir(phq)$_2$acac was 100:3, with a thickness of 10 nm), TmPyPB (1,3,5-tri[(3-pyridyl)-phen-3-yl]benzene, with a thickness of 42 nm), LiF (with a thickness of 0.5 nm), and Al (with a thickness of 120 nm) were subsequently formed on the PEDO:PSS film at 1×10$^{-6}$ Pa, obtaining the organic light-emitting device (6) after encapsulation. The materials and layers formed therefrom are described in the following:
ITO (150 nm)/PEDOT:PSS (45 nm)/TAPC (35 nm)/TCTA: Ir(phq)$_2$acac (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (6) were measured. The results are shown in Table 2.

Comparative Example 3: Fabrication of the Organic Light-Emitting Device (7) (Dry Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a ITV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, TAPC (di-[4-(N,N-ditolyl-amino)-phenyl]cyclohexane, with a thickness of 35 nm), TCTA (4,4',4''-tris (carbazol-9-yl)triphenylamine) doped with an organic metal compound Ir(piq)3(tris[1-phenylisoquinolinato-C2,N] iridium(III)) (the weight ratio between TCTA and Ir(piq)3 was 100:3, with a thickness of 10 nm), TmPyPB (1,3,5-tri [(3-pyridyl)-phen-3-yl]benzene, with a thickness of 42 nm), LiF (with a thickness of 0.5 nm), and Al (with a thickness of 120 nm) were subsequently formed on the PEDOT:PSS film at 1×10$^{-6}$ Pa, obtaining the organic light-emitting device (7) after encapsulation. The materials and layers formed therefrom are described in the following:
ITO (150 nm)/PEDOT:PSS (45 nm)/TAPC (35 nm)/TCTA: Ir(piq)$_3$ (3%, 10 nm)/TmPyPB (42 nm)/LiF (0.5 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (7) were measured. The results are shown in Table 2.

TABLE 2

| | organic metal compound | voltage (V) | brightness (cd/m$^2$) | current efficiency (cd/A) | power efficiency (lm/W) | C.I.E coordinate (x, y) | λmax (nm) |
|---|---|---|---|---|---|---|---|
| Example 16 | organic metal compound (I) | 4.1 | 1000 | 89.8 | 68.2 | (0.55, 0.45) | 580 |
| Example 17 | organic metal compound (II) | 3.8 | 1000 | 78.8 | 65.9 | (0.54, 0.45) | 576 |

TABLE 2-continued

| | organic metal compound | voltage (V) | brightness (cd/m²) | current efficiency (cd/A) | power efficiency (lm/W) | C.I.E coordinate (x, y) | λmax (nm) |
|---|---|---|---|---|---|---|---|
| Comparative Example 1 | compound PO-08 | 3.9 | 1000 | 60.1 | 48.4 | (0.49, 0.51) | 564 |
| Example 18 | organic metal compound (III) | 4.2 | 1000 | 41.8 | 31.3 | (0.64, 0.36) | 608 |
| Example 19 | organic metal compound (IV) | 5.5 | 1000 | 35.4 | 20.2 | (0.65, 0.35) | 616 |
| Comparative Example 2 | compound Ir(phq)$_2$acac | 4.5 | 1000 | 29.5 | 20.6 | (0.61, 0.39) | 596 |
| Comparative Example 3 | compound Ir(piq)$_3$ | 5.0 | 1000 | 11.6 | 7.3 | (0.66, 0.32) | 620 |

Example 20: Fabrication of the Organic Light-Emitting Device (8) (Wet Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes NPB (N,N'-bis(naphthalen-1-yl)-N,N'-bis(phenyl)-benzidine) and the organic metal compound (I), wherein the weight ratio of NPB and the organic metal compound (I) was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 55 nm). Next, LiF (with a thickness of 1 nm), and Al (with a thickness of 120 nm) were subsequently formed on the TmPyPB film at 1×10−6 Pa, obtaining the organic light-emitting device (8) after encapsulation. The materials and layers formed therefrom are described in the following:

ITO (150 nm)/PEDOT:PSS (45 nm)/NPB: organic metal compound (I) (30 nm)/TmPyPB (55 nm)/LiF (1 nm)/Al (120 nm)

Next, the optical properties (such as brightness (cd/m²), current efficiency (cd/A), power efficiency (lm/W), emission wavelength (nm), and C.I.E coordinates (x, y)) of the organic light-emitting device (8) were measured. The results are shown in Table 3.

Example 21: Fabrication of the Organic Light-Emitting Device (9) (Wet Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes NPB (N,N'-bis(naphthalen-1-yl)-N,N'-bis(phenyl)-benzidine) and the organic metal compound (II), wherein the weight ratio of NPB and the organic metal compound (II) was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 55 nm). Next, LiF (with a thickness of 1 nm), and Al (with a thickness of 120 nm) were subsequently formed on the TmPyPB film at 1×10−6 Pa, obtaining the organic light-emitting device (9) after encapsulation. The materials and layers formed therefrom are described in the following:

ITO (150 nm)/PEDOT:PSS (45 nm)/NPB: organic metal compound (II) (30 nm)/TmPyPB (55 nm)/LiF (1 nm)/Al (120 nm)

Next, the optical properties (such as brightness (cd/m²), current efficiency (cd/A), power efficiency (lm/W), emission wavelength (nm), and C.I.E coordinates (x, y)) of the organic light-emitting device (9) were measured. The results are shown in Table 3.

Example 22: Fabrication of the Organic Light-Emitting Device (10) (Wet Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes NPB (N,N'-bis(naphthalen-1-yl)-N,N'-bis(phenyl)-benzidine) and the organic metal compound (III), wherein the weight ratio of NPB and the organic metal compound (III) was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 55 nm). Next, LiF (with a thickness of 1 nm), and Al (with a thickness of 120 nm) were subsequently formed on the TmPyPB film at $1\times10^{-6}$ Pa, obtaining the organic light-emitting device (10) after encapsulation. The materials and layers formed therefrom are described in the following:

ITO (150 nm)/PEDOT:PSS (45 nm)/NPB: organic metal compound (III) (30 nm)/TmPyPB (55 nm)/LiF (1 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (10) were measured. The results are shown in Table 3.

Comparative Example 4: Fabrication of the Organic Light-Emitting Device (11) (Wet Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes NPB (N,N'-bis(naphthalen-1-yl)-N,N'-bis(phenyl)-benzidine) and the organic metal compound PO-08 (having a structure of

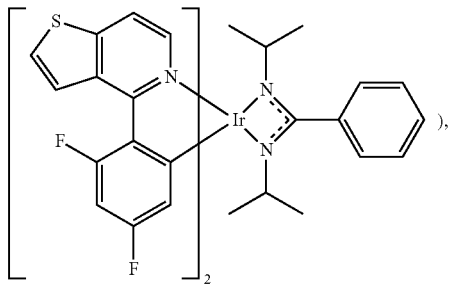

wherein the weight ratio of NPB and the organic metal compound PO-08 was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 55 nm). Next, LiF (with a thickness of 1 nm), and Al (with a thickness of 120 nm) were subsequently formed on the TmPyPB film at $1\times10^{-6}$ Pa, obtaining the organic light-emitting device (11) after encapsulation. The materials and layers formed therefrom are described in the following:

ITO (150 nm)/PEDOT:PSS (45 nm)/NPB: PO-08 (30 nm)/TmPyPB (55 nm)/LiF (1 nm)/Al (120 nm)

Next, the optical properties (such as brightness (cd/m$^2$), current efficiency (cd/A), power efficiency (lm/W), emission wavelength (nm), and C.I.E coordinates (x, y)) of the organic light-emitting device (11) were measured. The results are shown in Table 3.

Comparative Example 5: Fabrication of the Organic Light-Emitting Device (12) (Wet Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a ITV/ozone treatment for 30 min.

Next, PEDOT (poly(3,4)-ethylendioxythiophen):PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes NPB (N,N'-bis(naphthalen-1-yl)-N,N'-bis(phenyl)-benzidine) and the organic metal compound Ir(phq)$_2$acac (bis(2-phenylquinoline)(acetylacetonate)iridium(III)), wherein the weight ratio of NPB and the organic metal compound Ir(phq)2acac was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 55 nm). Next, LiF (with a thickness of 1 nm), and Al (with a thickness of 120 nm) were subsequently formed on the TmPyPB film at $1\times10^{-6}$ Pa, obtaining the organic light-emitting device (12) after encapsulation. The materials and layers formed therefrom are described in the following:

ITO (150 nm)/PEDOT:PSS (45 nm)/NPB: Ir(phq)$_2$acac (30 nm)/TmPyPB (55 nm)/LiF (1 nm)/Al (100 nm)

Next, the optical properties (such as brightness (cd/m$^2$), current efficiency (cd/A), power efficiency (lm/W), emission wavelength (nm), and C.I.E coordinates (x, y)) of the organic light-emitting device (12) were measured. The results are shown in Table 3.

Comparative Example 6: Fabrication of the Organic Light-Emitting Device (13) (Wet Process)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT (poly(3,4)-ethylendioxythiophen): PSS (e-polystyrenesulfonate) was coated on the ITO film by a blade and spin coating process (with a rotation rate of 2000 rpm) and baked at 130° C. for 10 min to form a PEDOT:PSS film serving as a hole injection layer (with a thickness of 45 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes NPB (N,N'-bis(naphthalen-1-yl)-N,N'-bis(phenyl)-benzidine) and the organic metal compound Hex-Ir(piq)$_3$ (tris[(4-n-hexylphenyl)isoquinoline]iridium(III)), wherein the weight ratio of NPB and the organic metal compound Hex-Ir(piq)3 was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 45 nm). Next, LiF (with a thickness of 1 nm), and Al (with a thickness of 100 nm) were subsequently formed on the TmPyPB film at $1\times10^{-6}$ Pa, obtaining the organic light-emitting device (13) after encapsulation. The materials and layers formed therefrom are described in the following:

ITO (150 nm)/PEDOT:PSS (45 nm)/TCTA: Hex-Ir(piq)$_3$ (30 nm)/TmPyPB (45 nm)/LiF (1 nm)/Al (100 nm)

Next, the optical properties (such as brightness (cd/m$^2$), current efficiency (cd/A), power efficiency (lm/W), emission wavelength (nm), and C.I.E coordinates (x, y)) of the organic light-emitting device (13) were measured. The results are shown in Table 3.

TABLE 3

| | organic metal compound | voltage (V) | brightness (cd/m$^2$) | current efficiency (cd/A) | power efficiency (lm/W) | C.I.E coordinate (x, y) | λmax (nm) |
|---|---|---|---|---|---|---|---|
| Example 20 | organic metal compound (I) | 3.2 | 1000 | 45.9 | 44.5 | (0.54, 0.45) | 580 |
| Comparative Example 4 | compound PO-08 | 3.9 | 1000 | 45.3 | 36.7 | (0.48, 0.51) | 564 |
| Example 21 | organic metal compound (II) | 4.2 | 1000 | 12.6 | 9.4 | (0.63, 0.37) | 604 |
| Example 22 | organic metal compound (III) | 4.3 | 1000 | 13.1 | 9.7 | (0.65, 0.35) | 616 |
| Comparative Example 5 | compound Ir(phq)$_2$ acac | 4.3 | 1000 | 16.6 | 12.3 | (0.60, 0.40) | 596 |
| Comparative Example 6 | compound Hex-Ir(piq)$_3$ | 4.5 | 1000 | 5.9 | 4.1 | (0.67, 0.33) | 620 |

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic metal compound, having a structure as defined by Formula (I):

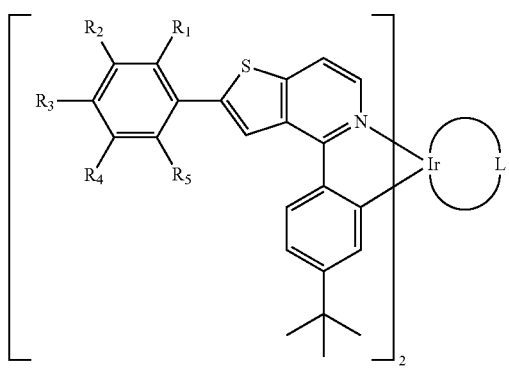

Formula (I)

wherein, $R_1$, $R_2$, $R_3$, $R_4$, and $R_5$ are independently hydrogen, halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

2. The organic metal compound as claimed in claim 1, wherein the halogen is fluorine.

3. The organic metal compound as claimed in claim 1, wherein the $C_{1-8}$ alkyl group is tert-butyl group.

4. The organic metal compound as claimed in claim 1, wherein the organic metal compound has a structure as defined by Formula (II):

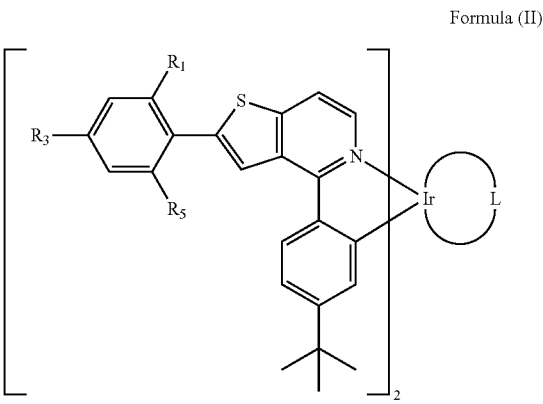

Formula (II)

wherein, $R_1$ and $R_5$ are independently hydrogen, halogen, $C_{1-8}$ alkyl group, or $C_{1-8}$ alkoxy group, $R_3$ is halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

5. The organic metal compound as claimed in claim 4, wherein the halogen is fluorine.

6. The organic metal compound as claimed in claim 4, wherein the $C_{1-8}$ alkyl group is tert-butyl group.

7. The organic metal compound as claimed in claim 1, wherein the organic metal compound has a structure as defined by Formula (III):

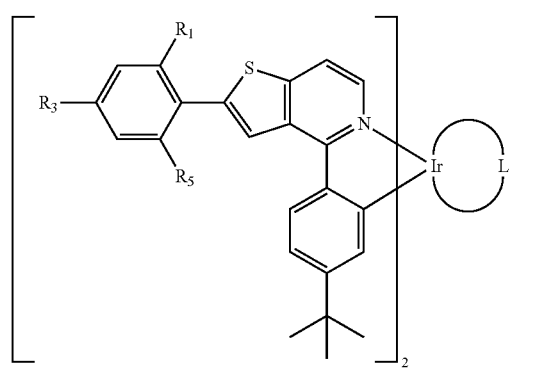

Formula (II)

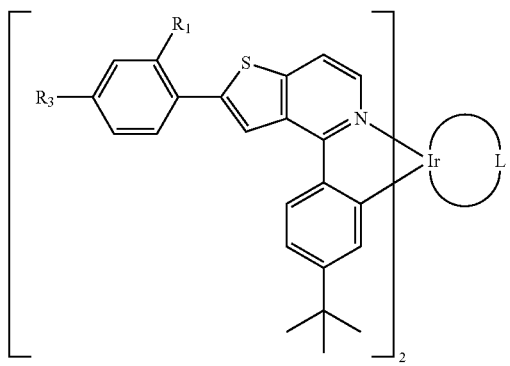

Formula (III)

wherein, $R_1$ is hydrogen, halogen, $C_{1-8}$ alkyl group, or $C_{1-8}$ alkoxy group, $R_3$ is halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

8. The organic metal compound as claimed in claim 7, wherein the halogen is fluorine.

9. The organic metal compound as claimed in claim 7, wherein the $C_{1-8}$ alkyl group is tert-butyl group.

10. An organic light-emitting device, comprising:
a pair of electrodes; and
an organic light-emitting element disposed between the electrodes, wherein the organic light-emitting element comprises an organic metal compound having a structure as defined by Formula (I):

Formula (I)

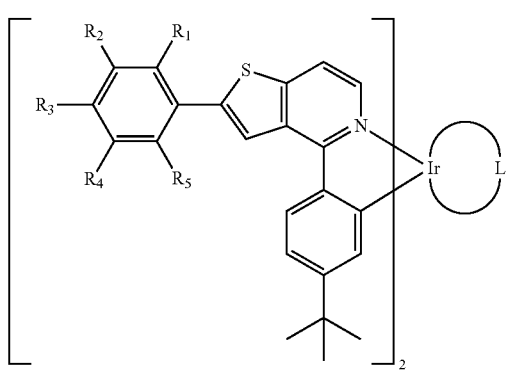

wherein, $R_1$, $R_2$, $R_3$, $R_4$, and $R_5$ are independently hydrogen, halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

11. The organic light-emitting device as claimed in claim 10, wherein the organic metal compound has a structure as defined by Formula (II):

wherein, $R_1$ and $R_5$ are independently hydrogen, halogen, $C_{1-8}$ alkyl group, or $C_{1-8}$ alkoxy group, $R_3$ is halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

12. The organic light-emitting device as claimed in claim 10, wherein the organic metal compound has a structure as defined by Formula (III):

Formula (III)

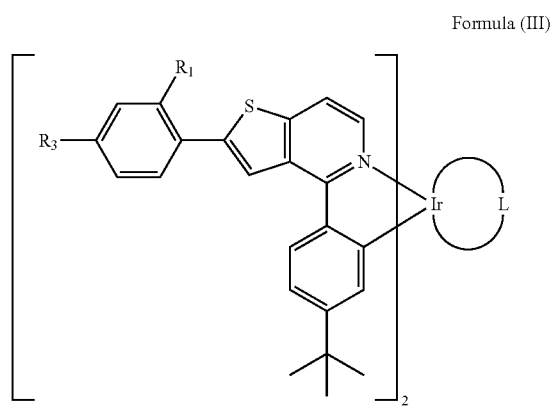

wherein, $R_1$ is hydrogen, halogen, $C_{1-8}$ alkyl group, or $C_{1-8}$ alkoxy group; $R_3$ is halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

13. The organic light-emitting device as claimed in claim 10, wherein the halogen is fluorine.

14. The organic light-emitting device as claimed in claim 10, wherein the $C_{1-8}$ alkyl group is tert-butyl group.

15. An organic light-emitting device, comprising:
a pair of electrodes; and
an organic light-emitting element disposed between the electrodes, wherein the organic light-emitting element comprises a light-emitting layer, and the light-emitting layer comprises a host material and a dopant material, and wherein the dopant material has a structure as defined by Formula (I):

Formula (I)

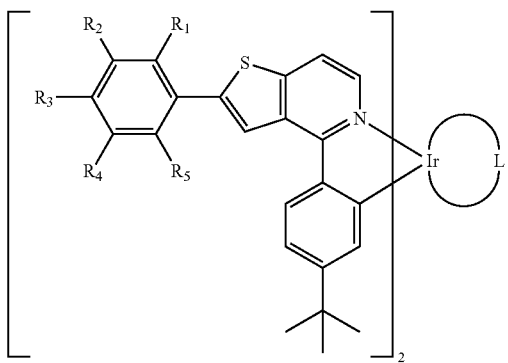

wherein, $R_1$, $R_2$, $R_3$, $R_4$, and $R_5$ are independently hydrogen, halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

16. The organic light-emitting device as claimed in claim 15, wherein the dopant material has a structure as defined by Formula (II):

Formula (II)

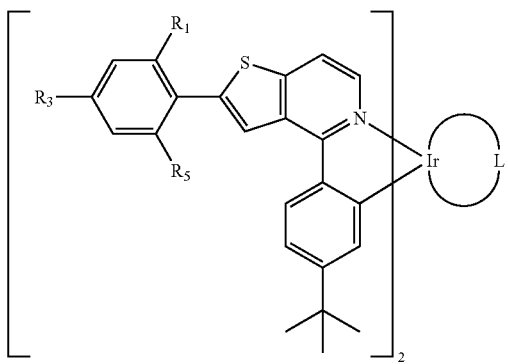

wherein, $R_1$ and $R_5$ are independently hydrogen, halogen, $C_{1-8}$ alkyl group, or $C_{1-8}$ alkoxy group, $R_3$ is halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

17. The organic light-emitting device as claimed in claim 15, wherein the dopant material has a structure as defined by Formula Formula (III)

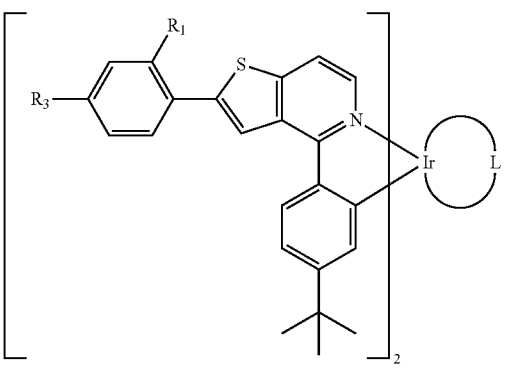

wherein, $R_1$ is hydrogen, halogen, $C_{1-8}$ alkyl group, or $C_{1-8}$ alkoxy group, $R_3$ is halogen, $C_{1-8}$ alkyl group, or $C_{1-8}$ alkoxy group; L is acetylacetone ligand, picolinic acid ligand, N, N'-diisopropylbenzamidinate ligand, or N, N'-diisopropyl-diisopropyl-guanidinate ligand.

18. The organic light-emitting device as claimed in claim 15, wherein the halogen is fluorine.

19. The organic light-emitting device as claimed in claim 15, wherein the $C_{1-8}$ alkyl group is tort-butyl group.

20. The organic light-emitting device as claimed in claim 15, wherein the organic light-emitting element emits red light or orange light under a bias voltage.

* * * * *